(12) United States Patent
Yoo et al.

(10) Patent No.: US 12,395,740 B2
(45) Date of Patent: Aug. 19, 2025

(54) METHOD, APPARATUS AND SYSTEM FOR CAPTURING IN VIVO IMAGES THROUGH DYNAMIC FOCUS MOTION COMPENSATION USING VARIABLE FOCUS LENS

(71) Applicants: KOREA ADVANCED INSTITUTE OF SCIENCE AND TECHNOLOGY, Daejeon (KR); Korea University Research and Business Foundation, Seoul (KR)

(72) Inventors: Hongki Yoo, Daejeon (KR); Minseok Jang, Daejeon (KR); Jin Won Kim, Seoul (KR); Joon Woo Song, Seoul (KR)

(73) Assignees: KOREA ADVANCED INSTITUTE OF SCIENCE AND TECHNOLOGY, Daejeon (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 18/624,266

(22) Filed: Apr. 2, 2024

(65) Prior Publication Data
US 2025/0150711 A1    May 8, 2025

(30) Foreign Application Priority Data
Apr. 5, 2023    (KR) .......................... 10-2023-0044700

(51) Int. Cl.
H04N 23/68    (2023.01)
A61B 5/00    (2006.01)
(Continued)

(52) U.S. Cl.
CPC ......... *H04N 23/687* (2023.01); *A61B 5/7285* (2013.01); *G02B 21/008* (2013.01); *H04N 23/66* (2023.01); *H04N 23/6811* (2023.01)

(58) Field of Classification Search
None
See application file for complete search history.

(56) References Cited

U.S. PATENT DOCUMENTS 6,480,285 B1 *    11/2002    Hill ...................... G02B 21/006
                                                          356/497
9,128,296 B2    9/2015    Steinborn et al.
(Continued)

OTHER PUBLICATIONS

Minseok Jang, "Electrocardiogram triggered motion compensation by dynamic focusing in intravital microscopy", Department of Mechanical Engineering, Korea Advanced Institute of Science and Technology, Korea, N7-4, C2 Seminar room, Dec. 26, 2022.
(Continued)

*Primary Examiner* — Daniel T Tekle
(74) *Attorney, Agent, or Firm* — LEX IP MEISTER, PLLC

(57) ABSTRACT

A method for capturing in vivo images by a control device which operates by at least one processor includes: acquiring 1dimensional (D) images acquired by scanning in vivo samples in one direction from a confocal microscopy including a focus variable lens; estimating motion information of the in vivo sample from the 1D images; generating a driving signal for synchronizing and varying a focal plane of the focus variable lens with a motion of the in vivo sample based on the estimated motion information, and controlling the focus variable lens with the driving signal; and acquiring, from the confocal microscopy, continuous images of the in vivo sample scanned in the focal plane varied according to the driving signal.

20 Claims, 24 Drawing Sheets

(51) Int. Cl.
  *G02B 21/00* (2006.01)
  *H04N 23/66* (2023.01)

(56) References Cited

U.S. PATENT DOCUMENTS

| | | | | |
|---|---|---|---|---|
| 2009/0105588 | A1* | 4/2009 | Emelianov | A61B 5/4869 606/27 |
| 2010/0268042 | A1* | 10/2010 | Wang | A61B 5/14546 73/587 |
| 2013/0123617 | A1* | 5/2013 | Sola i Caros | A61B 5/02125 600/490 |
| 2013/0217962 | A1* | 8/2013 | Date | A61B 1/045 600/103 |
| 2018/0199850 | A1* | 7/2018 | Lee | A61B 5/4041 |
| 2020/0342205 | A1* | 10/2020 | Park | G01N 21/6458 |
| 2022/0163779 | A1 | 5/2022 | Zou et al. | |
| 2024/0093289 | A1* | 3/2024 | Haase | C12Q 1/6869 |

OTHER PUBLICATIONS

Sara McArdle et al., "Intravital live cell triggered imaging system reveals monocyte patrolling and macrophage migration in atherosclerotic arteries", Journal of Biomedical Optics 20(2), 026005, Feb. 2015.

M. Bakalar et al., "Three-dimensional motion tracking for high-resolution optical microscopy, in vivo", Journal of Microscopy, vol. 246, Pt 3 2012, pp. 237-247, doi: 10.1111/j.1365-2818.2012.03613.x.

Wenjun Li et al., "Intravital 2-photon imaging of leukocyte trafficking in beating heart", J Clin Invest. 2012;122(7):2499-2508, Jul. 2012, doi:10.1172/JCI62970.

James L. Schroeder et al., "Subcellular Motion Compensation for Minimally Invasive Microscopy, In Vivo", Circulation Research. 2010:106:1129-1133, Feb. 18, 2010, DOI: 10.1161/CIRCRESAHA.109.211946.

Remco T. A. Megens et al., "In vivo high-resolution structural imaging of large arteries in small rodents using two-photon laser scanning microscopy", Journal of Biomedical Optics 15(1), 011108, Jan./Feb. 2010.

Sungon Lee et al., "In Vivo Microscope Image Stabilization through 3-D Motion Compensation using a Contact-type Sensor", 2008 IEEE/RSJ International Conference on Intelligent Robots and Systems Acropolis Convention Center, Nice, FR, Sep. 22-26, 2008.

Weiming Yu et al., "In vivo imaging of atherosclerotic plaques in apolipoprotein E deficient mice using nonlinear microscopy", Journal of Biomedical Optics 12(5), 054008, Sep./Oct. 2007.

Sungon Lee et al., "Image Stabilization for In Vivo Microscopy by High-Speed Visual Feedback Control", IEEE Transactions on Robotics, vol. 24, No. 1, Feb. 2008.

Amanda J. Wright et al., "Dynamic closed-loop system for focus tracking using a spatial light modulator and a deformable membrane mirror", Optics Express vol. 14, No. 1, Jan. 9, 2006.

Manuel Kunisch et al., "Active Axial Motion Compensation in Multiphoton-Excited Fluorescence Microscopy", arXiv 2401.10598v1 [physics.optics] Jan. 19, 2024.

* cited by examiner

↑ Carotid artery 2D image

↑ Carotid artery 1D scanning

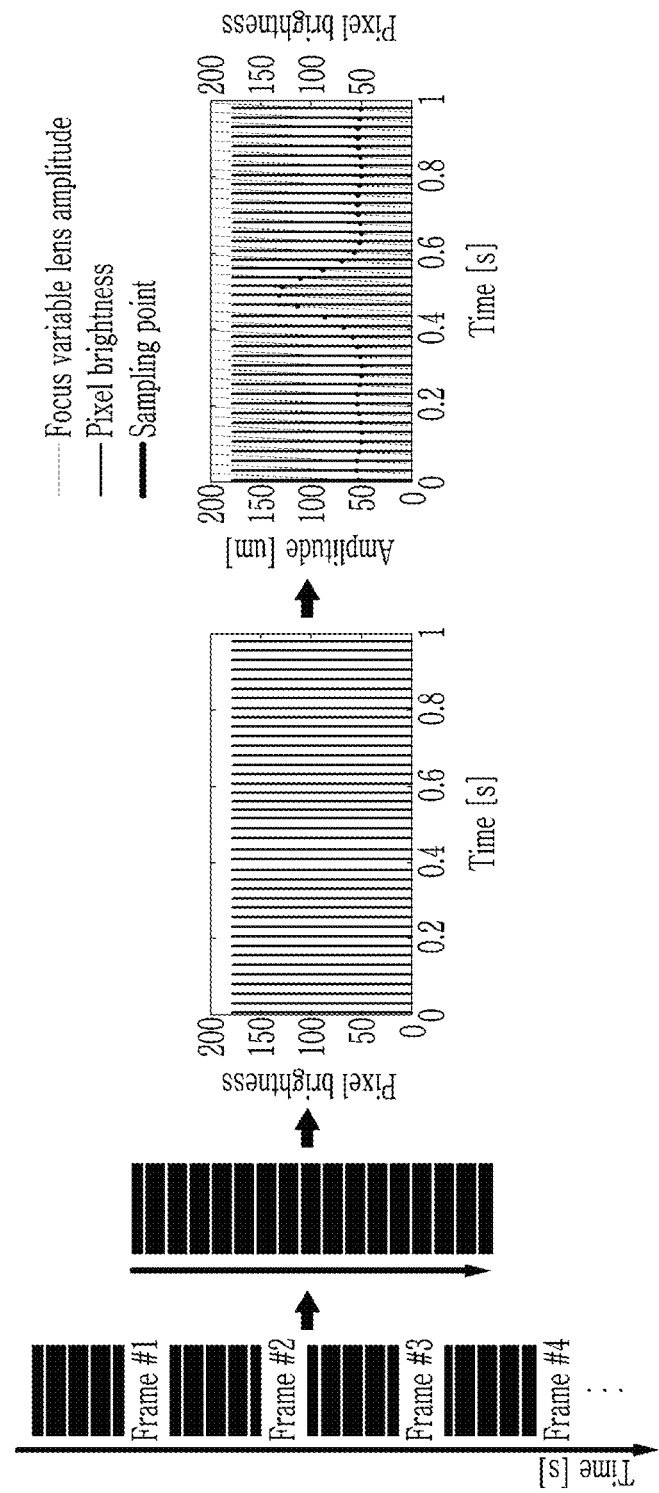

FIG. 15A
FIG. 15B
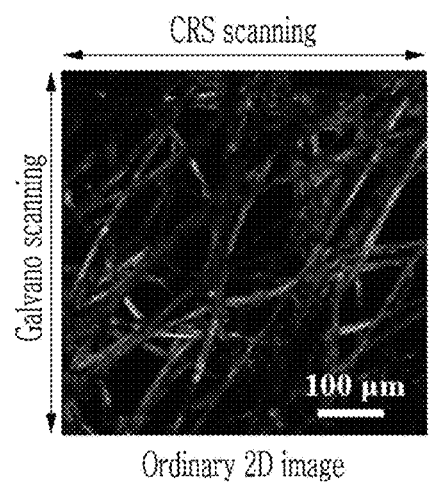
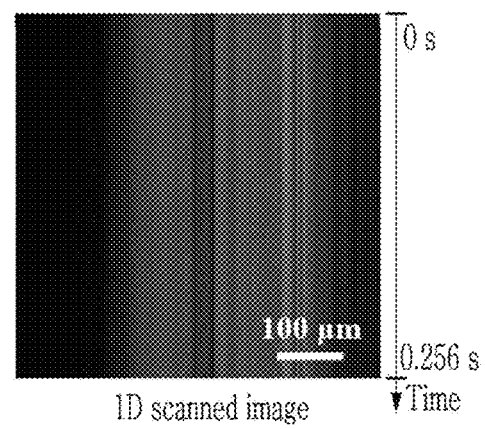
Ordinary 2D image
1D scanned image

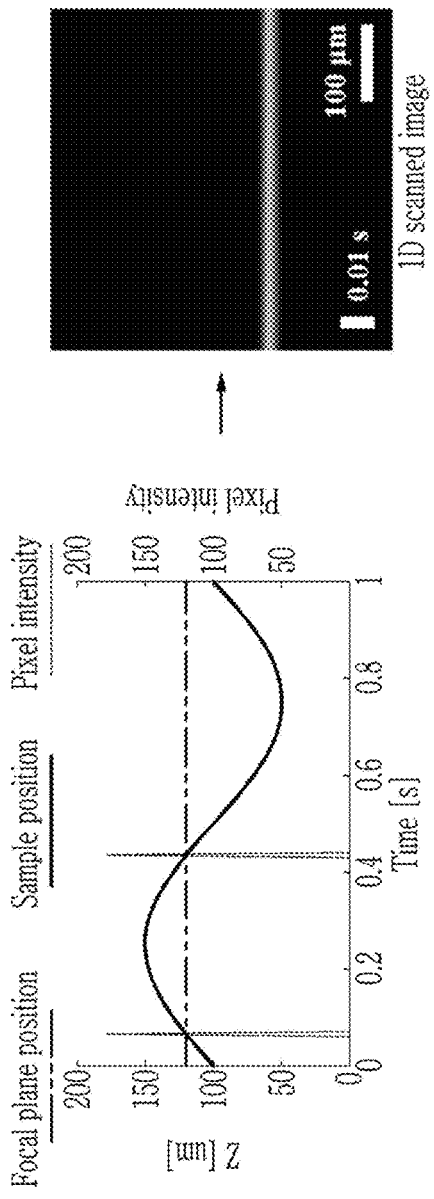
FIG. 16A
FIG. 16B
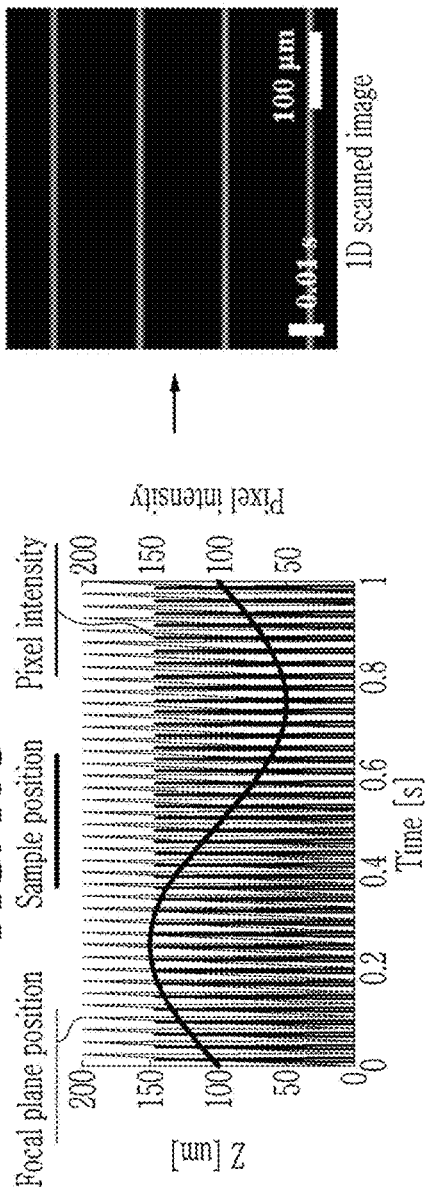
FIG. 16C
FIG. 16D

METHOD, APPARATUS AND SYSTEM FOR CAPTURING IN VIVO IMAGES THROUGH DYNAMIC FOCUS MOTION COMPENSATION USING VARIABLE FOCUS LENS

CROSS-REFERENCE TO RELATED APPLICATION

This application claims priority to and the benefit of Korean Patent Application No. 10-2023-0044700 filed in the Korean Intellectual Property Office on Apr. 5, 2023, the entire contents of which are incorporated herein by reference.

BACKGROUND

(a) Field

The present disclosure relates to a method, an apparatus and a system for capturing in vivo images through dynamic focus motion compensation using a variable focus lens.

(b) Description of the Related Art

An intravital microscopy is a technology that is actively utilized in cell tracking research and cell communication research in various institutions by enabling a cell-level high-resolution image to be acquired from a living animal.

In particular, the intravital microscopy has a characteristic that a minute environment such as pH, a temperature, etc., can maintained as it is in a natural state unlike ex vivo and in vitro, which contributes greatly to a cell biology field.

However, when the imaging in vivo, such as a rat carotid artery, proceeds for a living body, due to the movement of heartbeat, the focus of the microscopy continuously deviates from a sample, which is difficult to acquire a continuous image.

A variety of studies are proposed to compensate for such a problem, that is, the movement of deep breathing inevitably involved in the imaging in vivo.

A technology that directly contacts and stabilizes the tissue, which is one of the proposed technologies, can reduce the movement of the tissue itself, and can obtain high resolution images even in tissues such as heart and arteries, but there may be unintended blood flow obstruction.

In a technology that moves an objective lens while measuring the movement by using the sensor, one of the proposed technologies, a focal plane can follow the sample in real time, but a volume of a system is large.

An electrocardiogram (ECG) gating technology that acquires an image only in a section with small movement, one of the proposed technologies can acquire an image in which movement is compensated without a special device, but makes a loss in terms of a time resolution.

SUMMARY

The present disclosure attempts to provide a method, an apparatus and a system capable of scanning and estimating regular movement which occurs at each heartbeat cycle by measuring an electrocardiogram of a sample which is a living body, and capturing a high-resolution image of the sample while a tissue of the sample moves by moving a focus of a focus variable lens according to the estimated movement.

The present disclosure attempts to provide a method, an apparatus and a system which scan a sample at a high speed in an axial direction by attaching the focus variable lens to a back-focus plane of an objective lens of a confocal microscopy, and drive a focal plane of the focus variable lens according to the movement of the sample estimated through high-speed scanning.

An exemplary embodiment of the present disclosure provides a method for capturing in vivo images by a control device which operates by at least one processor, which includes: acquiring 1dimensional (D) images acquired by scanning in vivo samples in one direction from a confocal microscopy including a focus variable lens; estimating motion information of the in vivo sample from the 1D images; generating a driving signal for synchronizing and varying a focal plane of the focus variable lens with a motion of the in vivo sample based on the estimated motion information, and controlling the focus variable lens with the driving signal; and acquiring, from the confocal microscopy, continuous images of the in vivo sample scanned in the focal plane varied according to the driving signal.

In the estimating, an axial motion waveform of the in vivo sample is generated through the 1D images, and an axial amplitude cycle acquired from the axial motion waveform is estimated as the motion information.

The estimating may include generating one image acquired by frame-unit 1D images in a time-axis direction, acquiring pixel brightness information according to time from the merged image, and estimating the axial amplitude cycle of the in vivo sample by using sampling points which are points where the waveform of driving the focus variable lens and the pixel brightness information intersect when scanning the 1D images.

In the controlling, a driving signal generated by using waveform information of a predetermined unit cycle confirmed from the estimated motion information may be output to the focus variable lens.

In the controlling, a driving signal may be generated, in which a one-cycle waveform of the sample motion confirmed from the estimated motion information is converted into a voltage unit.

The method may further include, between the estimating and the controlling, receiving an electrocardiogram signal measured from the in vivo sample by an electrocardiogram measurement device, from the electrocardiogram measurement device, and in the controlling, the driving signal may be generated every heartbeat cycle acquired from the electrocardiogram signal, and output to the focus variable lens.

In the controlling, motion information of one cycle corresponding to the heartbeat cycle may be acquired from the estimated motion information of the in vivo sample, and a driving signal may be generated, in which the acquired motion information is converted into the voltage unit.

The focus variable lens may include an electrically tunable lens (ETL).

Another exemplary embodiment of the present disclosure provides a control device including: a memory storing instructions for performing an control operation for capturing an in vivo image; and at least one processor executing the instructions, in which the at least one processor acquires 1D images for scanning in vivo samples in one direction from a confocal microscopy including a focus variable lens, and estimates motion information of the in vivo sample from the 1D images, and controls the focus variable lens by using a driving signal for synchronizing and varying a focal plane of the focus variable lens generated based on the estimated motion information with the a motion of the in vivo sample, and acquires continuous images of the in vivo sample scanned on the focal plane varied according to the driving signal, from the confocal microscopy.

The at least one processor may analyze a heartbeat cycle from an electrocardiogram signal measured from the in vivo sample, and output the driving signal to the focus variable lens whenever the heartbeat cycle arrives.

The at least one processor may generate an axial motion waveform of the in vivo sample through the 1D images, and generate the driving signal by converting a one-cycle waveform corresponding to the heartbeat cycle into a voltage unit at an axial amplitude cycle acquired from the axial motion waveform.

The at least one processor may acquire pixel brightness information according to time from one image acquired by merging a plurality of frame-unit 1D images in a time-axis direction, and estimate axial motion information of the in vivo sample by using sampling points which are points where the waveform of driving the focus variable lens and the pixel brightness information intersect when scanning the 1D images.

Yet another exemplary embodiment of the present disclosure provides a system for capturing in vivo images, which includes: a confocal microscopy generating 1D images by scanning in vivo samples in one direction by using a focus variable lens; and a control device estimating motion information of the in vivo sample from the 1D images acquired from the confocal microscopy, generating a driving signal for synchronizing and varying a focal plane of the focus variable lens generated based on the estimated motion information with the a motion of the in vivo sample, controlling the focus variable lens with the driving signal, and acquiring continuous images of the in vivo sample scanned on the focal plane varied according to the driving signal, from the confocal microscopy.

The confocal microscopy may include the focus variable lens in which a focal plane is varied as a curvature radius is changed by input current, and a scanning module generating the 1D images for the in vivo sample through 1D scanning which drives only an X-axis scanner, and outputting the generated 1D images to the control device.

The confocal microscopy may further include an objective lens refracting light irradiated by a light source and passing through the focus variable lens, and guiding the refracted light to the in vivo sample, and absorbing light reflected on the in vivo sample, and delivering the absorbed light to the scanning module, and the focus variable lens may be attached to a back focus plane of the objective lens.

The system for capturing in vivo images may further include a photo multiplier tube converting optical signal type images acquired through a scan operation of the scanning module into an electrical signal, and outputs the converted images to the control device.

The control device may generate an axial motion waveform of the in vivo sample through the 1D images, and generate the driving signal by converting a predefined unit cycle waveform into a voltage unit at an axial amplitude cycle acquired from the axial motion waveform.

The system for capturing in vivo images may further include an electrocardiogram measurement device measuring an electrocardiogram (ECG) of the in vivo sample, and the control device may analyze a heartbeat cycle from an electrocardiogram signal received from the ECG measurement device, and output the driving signal to the focus variable lens whenever the heartbeat cycle arrives.

The control device may acquire pixel brightness information according to time from one image acquired by frame-unit 1D images in a time-axis direction, estimate the axial amplitude cycle of the in vivo sample by using sampling points which are points where the waveform of driving the focus variable lens and the pixel brightness information intersect when scanning the 1D images, and convert a one-cycle waveform corresponding to the heartbeat cycle during the estimated axial amplitude cycle into a voltage unit to generate the driving signal.

The system for capturing in vivo images may further include a data-signal integration device receiving the scanned images from the confocal microscopy, and delivering the received images to the control device, delivering the ECG signal received from the ECG measurement device to the control device, and outputting the driving signal to the focus variable lens.

According to an exemplary embodiment, axial motion of a sample can be estimated only with one focus variable lens without a direct contact with the sample, and a focal plane of the focus variable lens can be moved according to the estimated movement.

Further, since axial motion estimation of the sample is enabled by a non-contact scheme, it is possible to take advantage of in-vivo imaging as it is, and continuous images can also be acquired while the sample moves, thereby acquiring an image having an enhanced time resolution.

Further, a scheme of compensating a movement by repeated heartbeats by a scheme of estimating the axial motion of the sample by the non-contact scheme while scanning the sample with 1D scanning and the focus variable lens, and moving the focal plane according to an estimated waveform has no mechanical movement, so the scheme can be used along with a water immersion objective lens which is particularly required during in vivo imaging, and as a result, the scheme is expected to show a high utilization rate.

BRIEF DESCRIPTION OF THE DRAWINGS

FIGS. 5A, 5B and 5C are an exemplary diagram describing an axial amplitude estimation process of a sample according to an exemplary embodiment.

FIGS. 15A and 15B illustrate principles of a 1D scanned image.

FIGS. 16A, 16B, 16C and 16D are an exemplary diagram illustrating generation of a virtual 1D scanned image in a simulation.

DETAILED DESCRIPTION OF THE EMBODIMENTS

Figure 1:
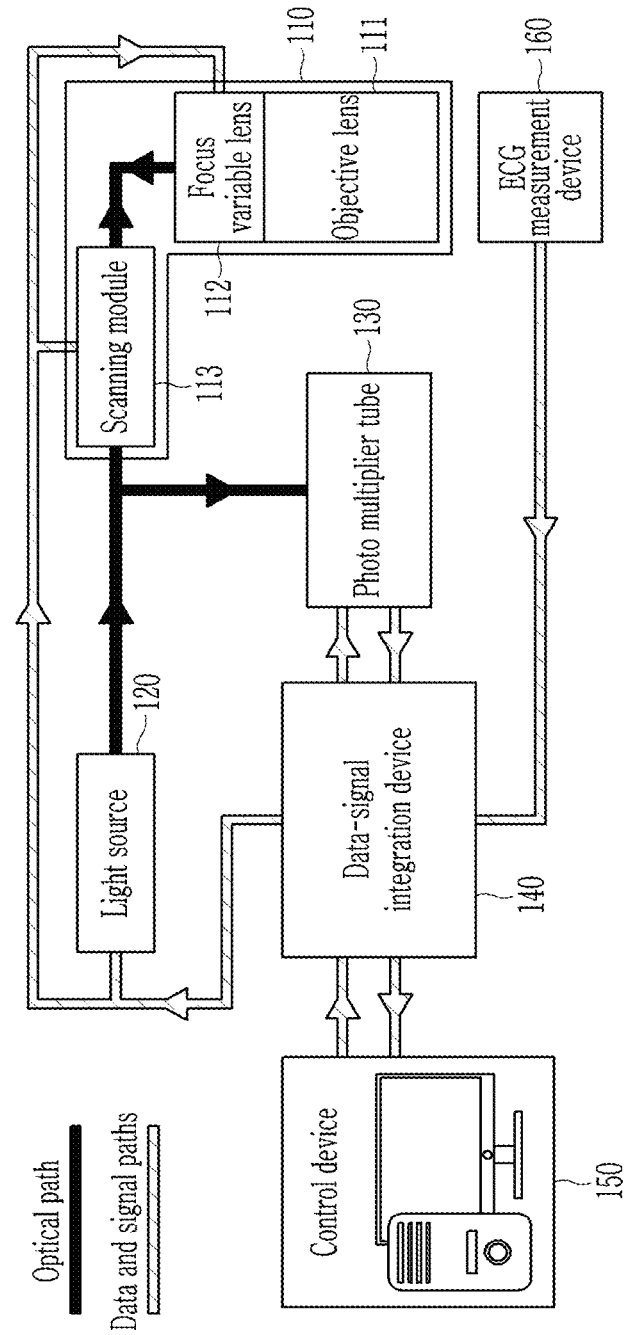
FIG. 1 is a configuration diagram of an in vivo image capturing system according to an exemplary embodiment.

In the following detailed description, only certain exemplary embodiments of the present disclosure have been shown and described, simply by way of illustration. However, the exemplary embodiments may be modified in various different ways, and are not limited to exemplary embodiments described herein. In addition, in the drawings, in order to clearly describe the present disclosure, a part not related to the description is not omitted and like reference numerals designate like elements throughout the present disclosure.

In addition, unless explicitly described to the contrary, the word "comprise", and variations such as "comprises" or "comprising", will be understood to imply the inclusion of stated elements but not the exclusion of any other elements.

In addition, the terms "-er", "-or" and "module" described in the specification mean units for processing at least one function and operation and can be implemented by hardware components or software components and combinations thereof.

Devices described in the present disclosure are constituted by hardware including at least one processor, a memory device, a communication device, etc., and a program executed in combination with the hardware is stored in a designated place. The hardware has a configuration and a performance which may execute the present disclosure. The program includes instructions implementing an operation method of the present invention and executes the present disclosure in link with hardware such as the processor and the memory device.

In this specification, "transmission or providing" may include indirectly transmitting or providing through another device or by using a bypass path in addition to direct transmission or providing.

In this specification, the expression described by the singular can be interpreted as a singular or plurality, unless an explicit expression such as "one" or "single" is used.

In this specification, regardless of the drawing, like reference numerals refer to like components throughout the specification and "and/or" includes respective mentioned components and all one or more combinations of the components.

In this specification, terms including an ordinary number, such as first and second, are used for describing various constituent elements, but the constituent elements are not limited by the terms. The terms are used only to discriminate one component from another component. For example, a first component may be referred to as a second component, and similarly, the second component may be referred to as the first component without departing from the scope of the present disclosure.

In this specification, in the flowchart described with reference to the drawings, the order of operations may be changed, multiple operations may be merged, or any operation may be divided, and a specific operation may not be performed.

The device of the present disclosure is a computing device configured and connected so that at least one processor may perform the operation of the present disclosure by executing instructions. The computer program may include instructions described for the processor to execute the operation of the present disclosure, and may be stored in a non-transitory computer readable storage medium. The computer program may be downloaded through a network or sold in a product form.

Figure 2:
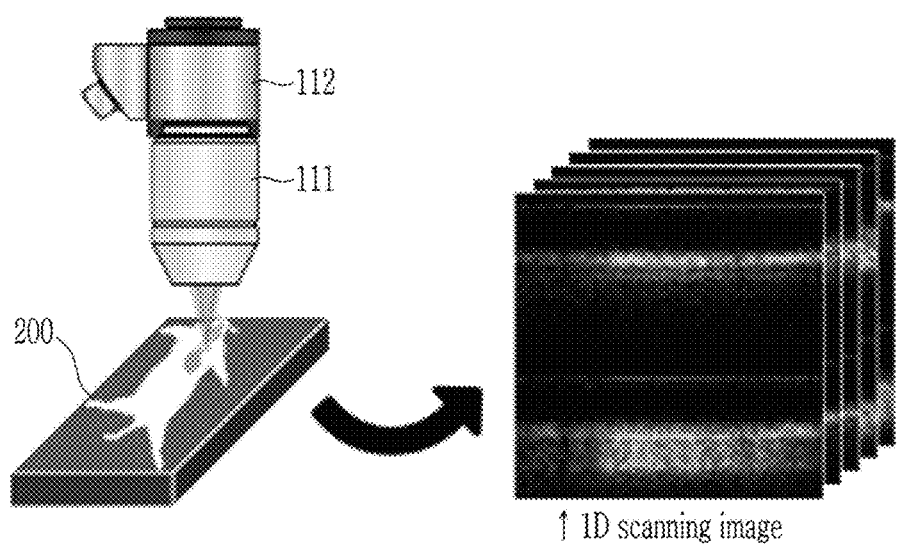
FIG. 2 illustrates a schematic structure of a confocal microscopy according to an exemplary embodiment

FIG. 1 is a configuration diagram of an in vivo image capturing system according to an exemplary embodiment, and FIG. 2 illustrates a schematic structure of a confocal microscopy according to an exemplary embodiment.

Referring to FIG. 1, the in vivo image capturing system 100 may compensate sample movement in an axial direction while capturing an in vivo image of a sample, and acquire an image less damaged by the sample movement.

The in vivo image capturing system 100 may compensate the sample movement in the axial direction through dynamic focusing by using a focus variable lens. That is, the in vivo image capturing system 100 may rapidly scan and estimate a regular movement which occurs at each heartbeat cycle with the focus variable lens by measuring an electrocardiogram (ECG) of the sample, and acquire a high-resolution in vivo image even while a tissue of the sample moves by moving a focus of the focus variable lens according to the estimated movement.

The in vivo image capturing system 100 may include a confocal microscopy 110, a light source 120, a photo multiplier tube 130, a data-signal integration device 140, a control device 150, and an electrocardiogram measurement device 160.

The confocal microscopy 110 is generally and often utilized in the intravital microcopy. The confocal microscopy 110 has a pinhole, so light which deviates from a focus does not pass through the pinhole, and only light which comes from the focus passes through the pinhole to increase a resolution of the confocal microscopy 110 and form optical sectioning. The optical sectioning may be a core in the confocal microscopy 110, and since the light which deviates from the focus is not detected, only a desired focal plane is enabled to be focused in a thick sample, and it becomes possible to acquire the image.

The confocal microscope 110 may include an objective lens 111, a focus variable lens 112, and a scanning module 113. Of course, components of the confocal microscopy 110 are not limited to the components 111, 112, and 113, but in the present disclosure, only a schematic configuration required for describing the exemplary embodiment is illustrated.

The objective lens 111 refracts light which is irradiated by the light source 120, and passes through the focus variable lens 112, and guides the light to a sample 200 of FIG. 2, and absorbs light reflected on the sample 200 of FIG. 2, and delivers the absorbed light to the scanning module 113.

Referring to FIG. 2, the focus variable lens 112 is attached to a back focal plane of the objective lens 111. When working is performed with the focus variable lens 112, it is important to select an optimal location of the focus variable lens 112 in the confocal microscopy 110 in order to minimize harmful effects. Upon considering characteristics of each component, when the focus variable lens 112 is disposed on the back focal plane of the objective lens 111, only minimal modification is required.

As the focus variable lens 112, an electrically tunable lens (ETL) may be used.

The focus variable lens 112 as a lens filled with a liquid may change a focal distance at a high speed as a curvature of a membrane is changed according to an intensity of pressing a lens surface membrane that surrounds the liquid. In the confocal microscopy 110, when an optical-axis-direction or axial-direction movement of the sample 200 is scanned rapidly by using the focus variable lens 112, a bright image may be acquired only at a moment of being in focus due to an optical sectioning ability of the confocal microscopy 110, so the axial-direction movement of the sample 200 may be estimated by applying the acquired bright image.

A focal plane formed by the focus variable lens 112 moves according to the movement of the sample 200. The focal plane of the focus variable lens 112 is varied according to a driving signal received from the data-signal integration device 140. That is, in the focus variable lens 112, the focal distance fluctuates according to the time during a unit cycle according to the driving signal.

The scanning module 113 adjusts a path of light emitted from the light source 120 to irradiate the light onto the sample 200. The light is irradiated to the sample 200 through the focus variable lens 112 and the objective lens 111, and then reflected on a focus formed at the sample 200 by the focus variable lens 112, and passes through the object lens 111 and the focus variable lens 112, and is incident on the scanning module 113.

The scanning module 113 generates an image of the sample 200 from an incident signal, and in this case, the sample 200 is scanned in the axial direction by using one mirror to generate the 1D scanned image.

The 1D scanned image includes information on the axial motion of the sample 200. In the 1D scanned image, a vertical axis becomes the time, and when the sample 200 is scanned in the axial direction by the focus variable lens 112, a moment when the focuses of the sample 200 and the confocal microscopy 110 according to the time are matched is included in the 1D scanned image.

The light source 120 may adopt various types including a laser.

The photo multiplier tube 130 converts an optical signal type 1D scanned image received from the scanning module 113 into an electrical signal, and output an electrical signal type 1D scanned image to the data-signal integration device 140.

The electrical signal type 1D scanned image is delivered to the control device 150 from the data-signal integration device 140.

The control device 150 estimates the axial motion of the sample 200 included in the 1D scanned image, i.e., an axial amplitude cycle of the sample 200. The control device 150 may generate a driving signal for controlling a focal plane to move every estimated axial amplitude cycle.

The control device 150 outputs the driving signal to the data-signal integration device 140. The data-signal integration device 140 outputs the driving signal to the focus variable lens 112. The focal plane of the focus variable lens 112 is varied according to the driving signal.

The driving signal is the form of a sawtooth wave or triangular wave. The driving signal scans the sample with a larger amplitude than the axial motion of the sample to control the movement of the sample 200 not to deviate from a scan range of the focus variable lens 112.

The ECG measurement device 160 measures electricity flowing through the heart of a biometric sample 200. The ECG measurement device 160 transmits a measured ECG signal to the data-signal integration device 140. The data-signal integration device 140 delivers the received ECG signal to the control device 150.

When the ECG signal is delivered to the control device 150, the control device 150 examines a wave of the ECG signal to generate an electrical pulse for each R-peak of the ECG signal. The electrical pulse is a heartbeat signal.

The control device 150 generates the driving signal for each heartbeat cycle, and outputs the generated driving signal to the data-signal integration device 140. That is, the heartbeat signal is used as a trigger signal for generating the driving signal. Accordingly, whenever the ECG signal is generated from the sample, the driving signal may be output to the focus variable lens 112.

Figure 3:
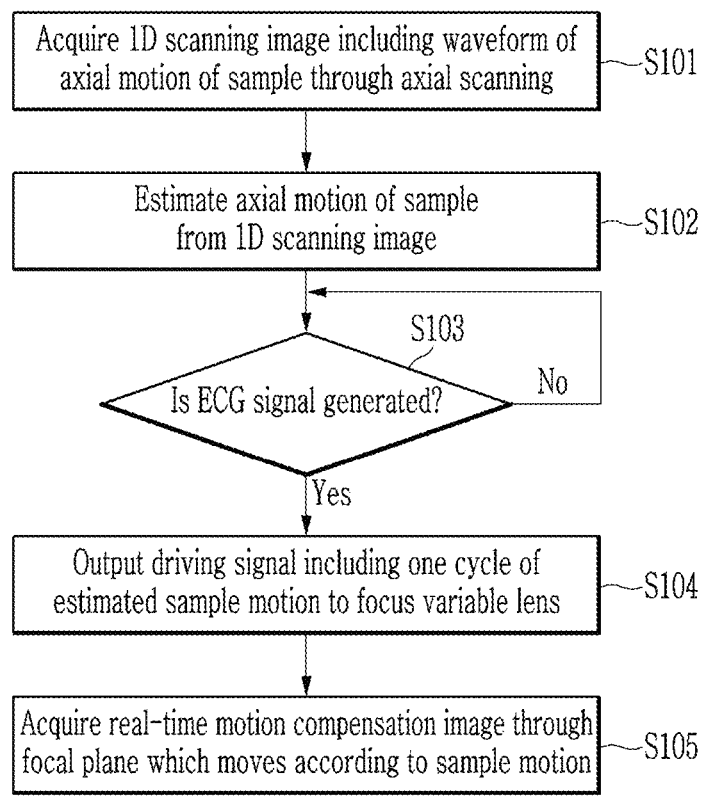
FIG. 3 is a flowchart describing an operation of an in vivo image capturing system according to an exemplary embodiment.
Figure 4A:
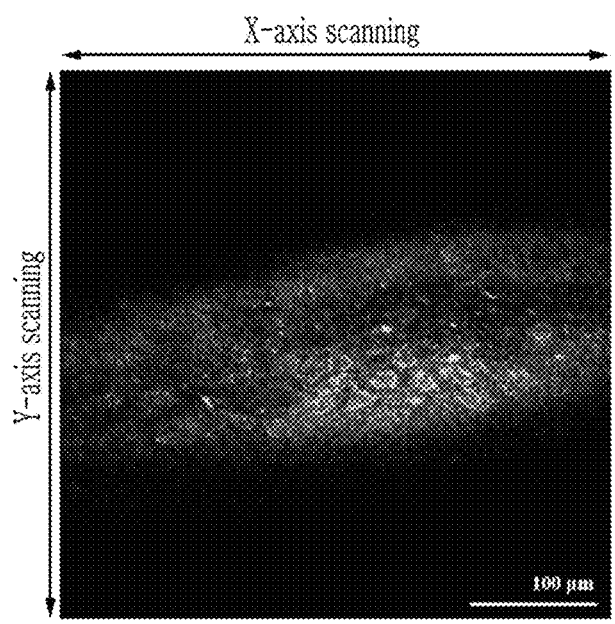
FIGS. 4A and 4B are a diagram describing 1D scanning according to an embodiment.
Figure 4B:
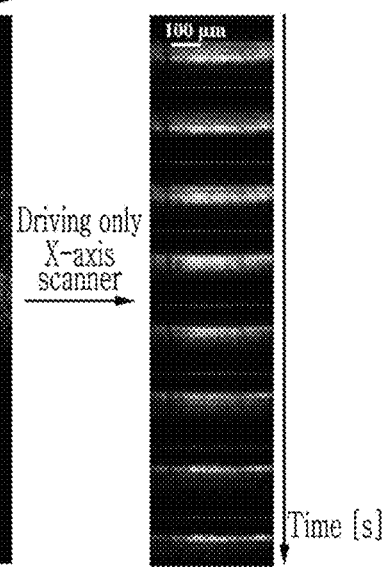
Figure 6:
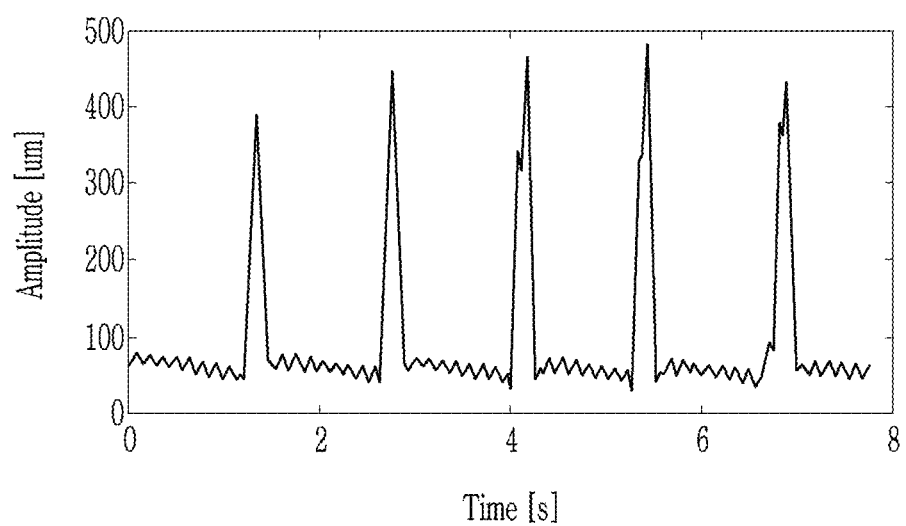
FIG. 6 is an exemplary diagram illustrating a movement estimation result of a sample according to an exemplary embodiment.
Figure 7:
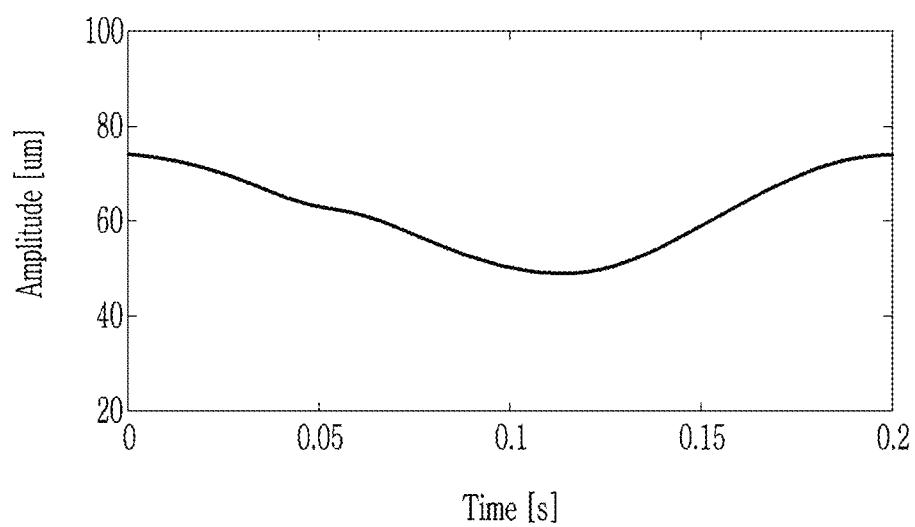
FIG. 7 is an exemplary diagram illustrating a one-cycle waveform of heartbeat movement according to an embodiment.
Figure 8:
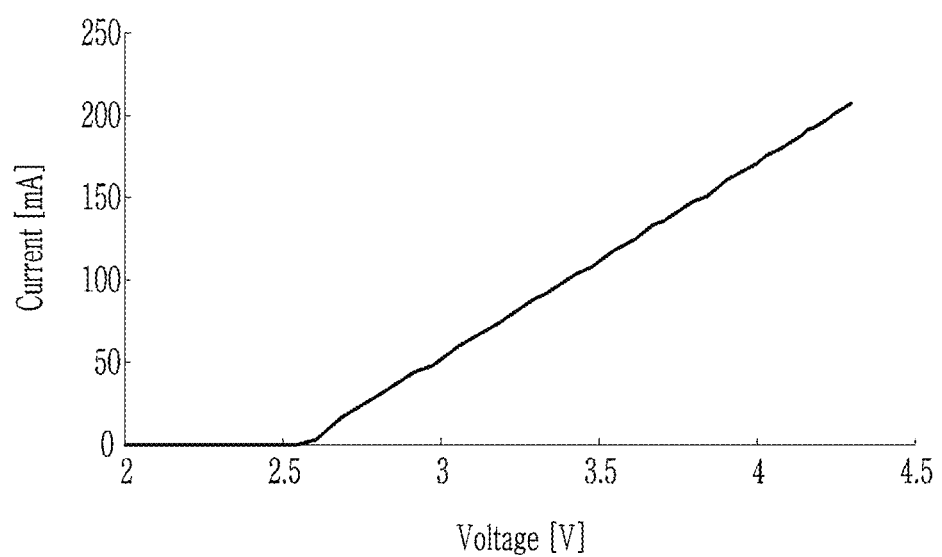
FIG. 8 is a graph illustrating a relationship between analog input voltage and current applied to a focus variable lens according to an exemplary embodiment.
Figure 9:
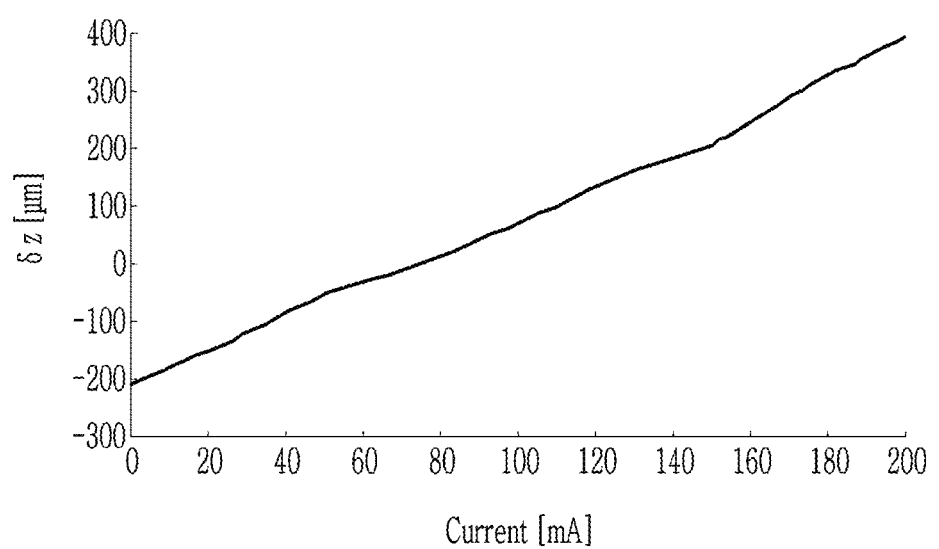
FIG. 9 is a graph illustrating a relationship between input current and a focal plane of the focus variable lens according to an exemplary embodiment.
Figure 10:
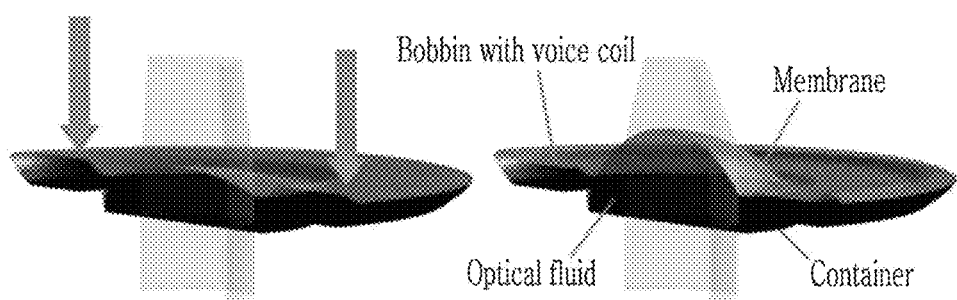
FIG. 10 is a structural diagram of an ETL according to an exemplary embodiment.
Figure 11:
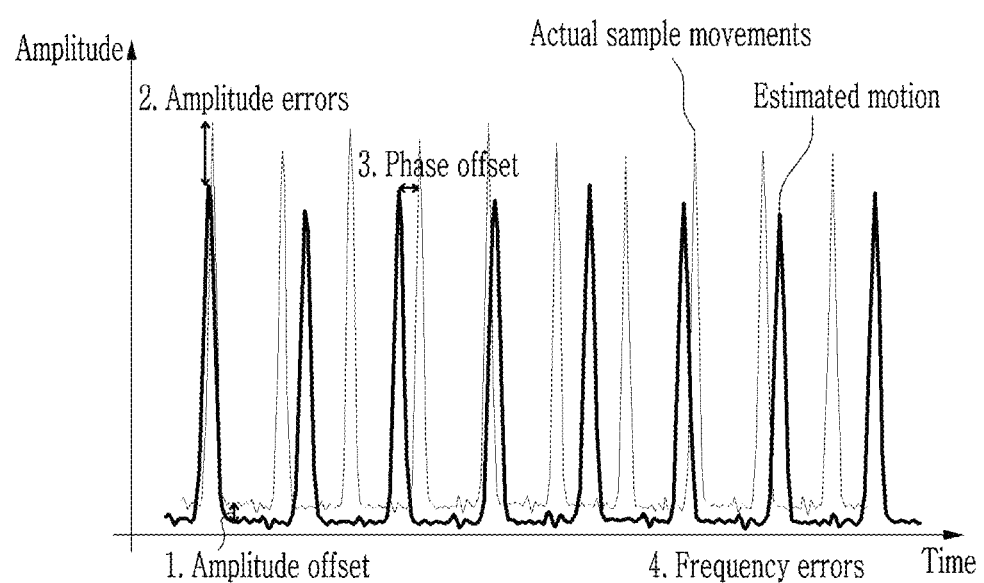
FIG. 11 illustrates four types of errors causing a difference between an actual sample movement and an estimated sample movement.
Figure 12:
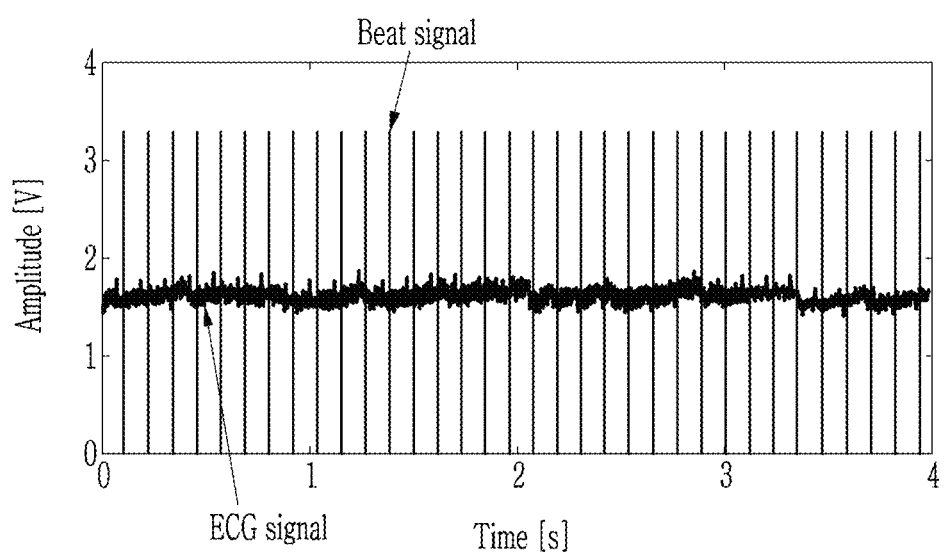
FIG. 12 is a graph illustrating an electrocardiogram signal and a heartbeat signal according to an exemplary embodiment.
Figure 13:
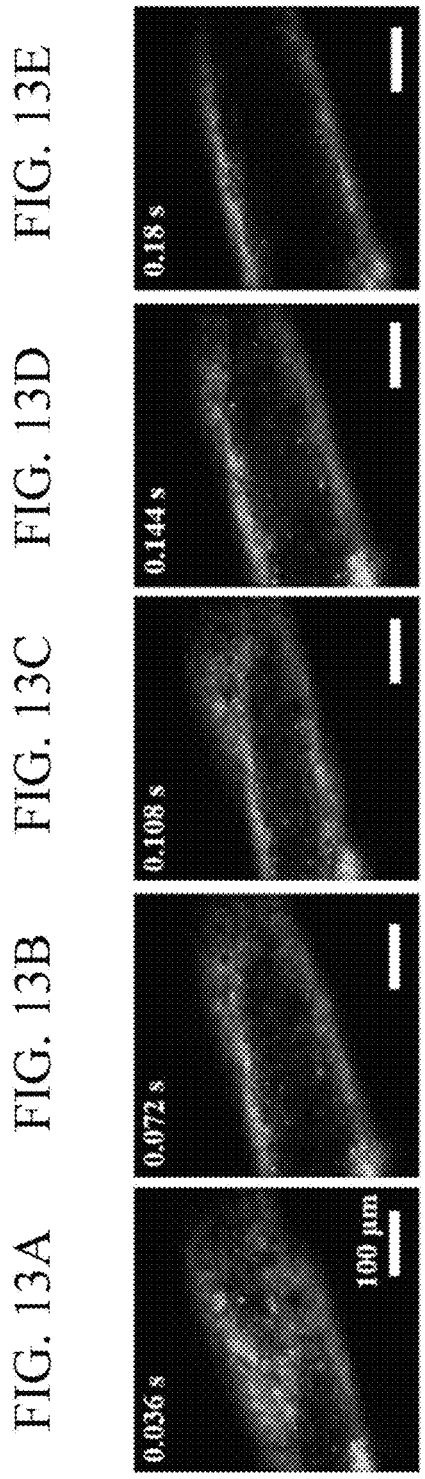
FIGS. 13A, 13B, 13C, 13D and 13E illustrate a real-time sample image in which axial motion is compensated according to an embodiment.

FIG. 3 is a flowchart describing an operation of an in vivo image capturing system according to an exemplary embodiment, FIGS. 4A and 4B are a diagram describing 1D scanning according to an embodiment, FIGS. 5A, 5B and 5C are an exemplary diagram describing an axial amplitude estimation process of a sample according to an exemplary embodiment, FIG. 6 is an exemplary diagram illustrating a movement estimation result of a sample according to an exemplary embodiment, FIG. 7 is an exemplary diagram illustrating a one-cycle waveform of heartbeat movement according to an embodiment, FIG. 8 is a graph illustrating a relationship between analog input voltage and current applied to a focus variable lens according to an exemplary embodiment, FIG. 9 is a graph illustrating a relationship between input current and a focal plane of the focus variable lens according to an exemplary embodiment, FIG. 10 is a structural diagram of an ETL according to an exemplary embodiment, FIG. 11 illustrates four types of errors causing a difference between an actual sample movement and an estimated sample movement, FIG. 12 is a graph illustrating an electrocardiogram signal and a heartbeat signal according to an exemplary embodiment, and FIGS. 13A, 13B, 13C, 13D and 13E illustrate a real-time sample image in which axial motion is compensated according to an embodiment.

Referring to FIG. 3, a procedure in which the control device 150 of the in vivo image capturing system 100 compensates the movement of the sample in link with other components 110, 120, 130, 140, and 160 is described.

The control device 150 performs a 3-step movement compensation procedure.

The 3-step movement compensation procedure is constituted by an axial motion probing mode, a movement estimation mode, and a movement compensation mode.

S101 is an operation of the axial motion probing mode, S102 is an operation of the movement estimation mode, and S103 to S105 are operations of the movement compensation mode. The in vivo image capturing system 100 may reduce motion artifacts of the in vivo image during the continuous processes S101 to S105, that is, acquiring an image through dynamic focusing by using the focus variable lens 112 of FIG. 1.

In the axial motion probing mode, the control device 150 acquires the 1D scanned image through 1D scanning, and high-speed axial scanning using the focus variable lens 112 of FIG. 1.

In this case, the control device 150 outputs a scan waveform for the 1D scanning to the focus variable lens 112 of FIG. 1 to drive the focus variable lens 112 of FIG. 1. In this case, the scan waveform is the sawtooth wave or the triangular wave, and is set to have an amplitude to scan the sample 200 of FIG. 2 with a larger amplitude than the axial motion of the sample 200 of FIG. 2. Therefore, the movement of the sample 200 of FIG. 2 is prevented from deviating from the scan range of the focus variable lens 112 of FIG. 1.

The 1D scanning is to acquire the image by driving only one of two scanners used when forming a 2D image.

Referring to FIG. 4A, basically, a carotid artery 2D image of the sample is acquired by simultaneously performing X-axis scanning and Y-axis scanning.

On the contrary, referring to FIG. 4B, in an exemplary embodiment of the present disclosure, the 1D scanned image may be acquired through carotid artery 1D scanning by driving only an X-axis scanner. In this case, a vertical axis is a time s.

In this case, the 1D scanned image includes the information on the axial motion of the sample 200 of FIG. 2, that is, a waveform of the axial motion.

In the movement estimation mode, the control device 150 estimates an axial amplitude cycle of the sample 200 from the axial motion waveform of the sample 200 included in the 1D scanned image (S102).

According to an exemplary embodiment, a customized movement estimation algorithm programmed in MATLAB and LabVIEW may be used in S102. MATLAB is engineering software that provides numerical interpretation and a programming environment developed by Mathworks. LabVIEW is a system design platform and a development environment for a visual programming language of National Instruments. A result of the movement estimation algorithm may be stored in a MATLAB code text file or a LabVIEW code TDMS file.

Referring to FIG. 5A, the control device 150 generates one image acquired by merging a plurality of frame-unit 1D scanned images in a time-axis direction. As such, in one merged image, a plurality of continuous 1D scanned images are jointly disposed on a time axis.

Referring to FIG. 5B, the control device 150 may acquire information on a pixel brightness (or pixel intensity) according to the time from the merged image. The pixel brightness is acquired on vertical lines of the merged image.

Referring to FIG. 5C, the control device 150 may generate a sampling point at a point where the pixel brightness becomes the maximum by matching a focus variable lens amplitude waveform with the pixel brightness. That is, the control device 150 may acquire a sampling point illustrated in FIG. 5C when the pixel brightness expressed in FIG. 5B and an amplitude of a waveform of driving the focus variable lens 112 of FIG. 1 are matched with each other.

Since the control device 150 knows information on an input signal for the focus variable lens 112 of FIG. 1, e.g., the waveform, the amplitude, and the frequency, the control device 150 may express a focal plane location, i.e., the focus variable lens amplitude as a sawtooth waveform.

A point where the focal plane location and the pixel brightness intersect includes movement information of the sample. A maximum value of the pixel brightness is reached only while the location and the focal plane of the sample are matched, so an intersection point of a focal plane change and a temporal pixel brightness change derived by the focus variable lens 112 of FIG. 1 becomes a sampling point of a sample waveform.

Accordingly, the control device 150 may correspondingly estimate the axial motion of the sample 200 of FIG. 2 as illustrated in FIG. 6 through the sampling point. The axial motion is expressed as a change of the amplitude according to the time.

Referring to FIG. 6, an example in which a normal Balb/c mice is used as the sample 200 of FIG. 2 is illustrated. The movement of the heartbeat of the carotid artery of the sample 200 of FIG. 2 corresponds to a small amplitude of approximately 10 Hz, and largely moving at an interval of approximately 2 seconds indicates a result of movement by breathing.

As described above, the movement by breathing also exists in the carotid artery of the sample 200 of FIG. 2. Accordingly, by selecting only an interval where the movement by the heartbeat exists in a waveform of a restored sample 200 of FIG. 2, a one-cycle waveform illustrated in FIG. 7 may be acquired. The one-cycle waveform of the heartbeat movement is generated as a driving signal converted into a voltage unit, and provided to the focus variable lens 112 of FIG. 1.

Referring back to FIG. 3, the control device 150 determines whether the ECR signal transmitted by the ECG measurement device 160 is received from the data-signal integration device 140 (S103).

When it is determined that the ECG signal is received in S103, the control device 150 outputs a driving signal including one cycle of the sample movement estimated in S102 to the focus variable lens 112 of FIG. 1 (S104).

The control device 150 generates the driving signal including one cycle of the sample movement estimated in S102, and outputs the generated signal to the data-signal integration device 140, whenever every heartbeat signal is generated. The data-signal integration device 140 outputs the driving signal to the focus variable lens 112 of FIG. 1.

In S104, the control device 150 may generate a driving signal which converts the one-cycle waveform of the sample movement estimated in S102 into the voltage unit.

Referring to FIG. 8, a relationship between analog input voltage and current applied to the focus variable lens 112 of FIG. 1 is illustrated.

Referring to FIG. 9, a relationship between input current and a focal plane change is illustrated. Input current of 0 mA to 75 mA provides a negative focal distance forming a focal plane which is separated farther from a focal plane before inserting the focus variable lens 112 of FIG. 1.

Input current of 75 mA to 300 mA provides a positive focal distance to form the focal plane at a location closer to the objective lens 111 of FIG. 1.

Referring to FIGS. 8 and 9, the location of the focal plane may be confirmed from current matched with the driving signal converted into the voltage signal.

In S104, the control device 150 may linearly multiply a one-cycle waveform of a sample movement for a distance of a micrometer (μm) unit estimated in S102 by FIGS. 8 and 9 illustrating a look-up table experimentally acquired through the focus variable lens 112, and convert the one-cycle waveform into the voltage unit.

A process of converting the one-cycle waveform into the voltage unit through FIGS. 8 and 9 is described below.

FIG. 8 illustrates current delivered to the focus variable lens 112 of FIG. 1 according to analog output voltage, and a relationship between two physical amounts displayed in FIG. 8 may be defined as a linear equation as in Equation 1.

$$I = 118.67V - 303.16 \quad \text{(Equation 1)}$$

In this case, I and V represent current and voltage, respectively.

FIG. 9 illustrates a relationship between distances in which the focal plane moves in a vertical direction (i.e., axial direction) according to the current input into the focus variable lens 112 of FIG. 1, and may be defined as the linear equation as in Equation 2.

$$\delta z = 2.9461 - 213.76 \quad \text{(Equation 2)}$$

In this case, δz and I represent a distance in which the focal plane moves due to the focus variable lens 112 of FIG. 1, and current, respectively.

Accordingly, when parameter current I is eliminated from the linear equation in FIGS. 8 and 9, a linear equation for the voltage and a focal plane movement distance, i.e., a linear equation shown in Equation 3 may be acquired.

$$V = 2.86 \times 10^{-3} \delta z + 3.166 \quad \text{(Equation 3)}$$

When an axial amplitude value of a sample movement represented as a unit of the distance acquired in FIG. 7 is substituted in the linear equation, a voltage value corresponding to each data point (sampling point) constituting the sample movement corresponds to the axial amplitude value. By such a scheme, the one-cycle waveform of FIG. 7 may be converted into the voltage unit.

As such, the driving signal which converts the one-cycle waveform into the voltage unit is delivered to the data-signal integration device 140 to allow the focus variable lens 112 of FIG. 1 to move according to the one-cycle waveform.

Referring to FIG. 10, a structure of an electrically tunable lens (ETL) used as the focus variable lens 112 of FIG. 1 is illustrated.

The ETL is a liquid lens covered with two membranes. Sophisticated current control using a voice coil actuator changes a curvature radius of a lens surface by pressing the membrane.

The input current controls a pressure applied to a bobbin with a voice coil, which changes a curvature radius of an upper lens membrane with the ETL.

Accordingly, when the driving signal including the one-cycle waveform of the sample movement converted into the voltage signal is provided to the ETL, a current signal matched with the voltage signal changes the curvature radius of the upper lens membrane, and as a result, the focal plane may be varied according to the sample movement.

Referring to FIG. 11, there is a difference between actual sample movements and an estimated motion.

When a scanning image acquisition time in the axial motion probing mode and a focal plane change in the movement compensation mode are not the same as each other, and it is difficult to match start moments of two independent signals, so an estimated sample movement waveform is different from an actual sample movement waveform. Four types of errors which cause such a difference include "1. Amplitude Offset", "2. Amplitude errors", "3. Phase offset", and "4. Frequency errors".

According to FIG. 5C, it is assumed that when the pixel brightness and the focal plane location according to the time are matched, start points thereof are started to be the same. A calculation is wrong in the sawtooth waveform of the focus variable lens 112 of FIG. 1 due to an error of the start point, and as a result, the estimated sample movement waveform moves in the axial direction, so an amplitude offset occurs. The amplitude offset may be easily controlled by manually moving a sample stage.

An amplitude error occurs due to an irregular amplitude of the sample movement in in vivo imaging, but is not a fluctuation amount that significantly reduces a movement estimation performance.

A most important variable which exerts a larger influence on the sample movement estimation performance is a phase offset and a frequency error.

When a phase is not matched with an actual sample movement, it is difficult to acquire an image in which the sample movement is corrected. Further, when the frequency is not the same as the sample movement, the phase offset varies depending on the time. Accordingly, it is important to reflect a real-time frequency of the actual sample movement, and a timing signal for each ECG cycle is required to reflect the real-time frequency.

Referring to FIG. 12, the control device 150 analyzes a waveform of the ECG signal received from the ECG measurement device 160 to analyze a heartbeat signal. The heartbeat signal represents an electrical wave which makes the heartbeat, and when the wave is examined, the heartbeat may be measured, and the heartbeat signal illustrated in FIG. 12 may be generated through a heart rate.

As such, the heartbeat signal is acquired during acquisition of the ECG signal, and focal plane movement for the focus variable lens 112 of FIG. 1 is triggered. Accordingly, the focal plane movement of the focus variable lens 112 of FIG. 1 may be matched with the movement and the frequency of the actual sample, and after the frequencies are matched, repeated errors occur, so the phase offset may be manually set.

As such, a frequency error may be solved by using the ECG signal as the trigger signal of the output of the driving signal, and a user may solve the amplitude offset, the amplitude error, and the phase error through adjustment while viewing an image acquired in real time.

Consequently, the axial motion of the sample 200 of FIG. 2 may be known only with the 1D scanned image, and the focal plane of the focus variable lens 112 of FIG. 1 is moved according to the estimated sample waveform to compensate the movement by the heartbeat which exists upon the in vivo imaging.

The focus variable lens 112 of FIG. 1 varies the focal plane is varied according to the driving signal received in S104. Accordingly, the control device 150 allows the focal plane to move according to the sample movement to acquire the in vivo image of the sample compensated according to the sample movement (S105).

Referring to FIGS. 13A, 13B, 13C, 13D, and 13E, the control device 150 may acquire images at a moment when the movement and the focal plane of the sample 200 of FIG. 2 are matched every cycle of 0.036 s.

As such, in the confocal microscopy 110 of FIG. 1, when an optical-axis-direction (or axial-direction) movement of the sample 200 of FIG. 2 is scanned rapidly by using the focus variable lens 112 of FIG. 1, a bright image may be acquired only at a moment of being in focus due to an optical sectioning ability of the confocal microscopy 110 of FIG. 1, so the axial-direction movement of the sample 200 of FIG. 2 may be estimated by applying the acquired bright image.

Accordingly, the axial motion of the sample 200 of FIG. 2 may be known only with the 1D scanned image, and the focal plane of the focus variable lens 200 of FIG. 1 is moved according to the estimated waveform of the sample 200 of FIG. 2 to compensate the movement by the heartbeat which exists upon the in vivo imaging.

Figure 14:
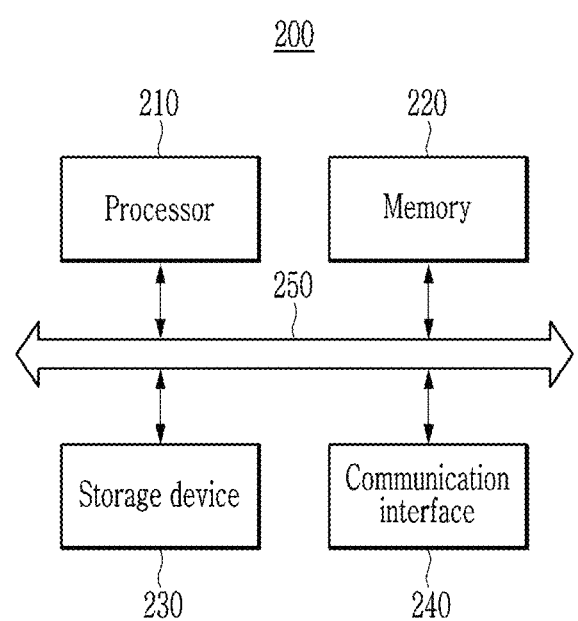
FIG. 14 is a configuration diagram of a computing device according to an exemplary embodiment.

FIG. 14 is a configuration diagram of a computing device according to an exemplary embodiment.

Referring to FIG. 14, the data-signal integration device 140 and/or the control device 150 described in FIGS. 1 to 13 may be implemented as a computing device 200 that operates by at least one processor.

The computing device 200 may include one or more processors 210, a memory 220 that loads a computer program performed by the processor 210, a storage device 230 that stores the computer program and various data, a communication interface 240, and a bus 250 connecting them. Besides, the computing device 200 may further include various components.

The processor 210, as a device that controls the operation of the computing device 200, may be various types of processors that process instructions included in the computer program, and for example, may be configured to include a central processing unit (CPU), a microprocessor unit (MPU), a micro controller unit (MCU), a graphic processing unit (GPU), or any type of processor well-known in a technical field of the present disclosure.

The memory 220 stores various types of data, instructions, and/or information. The memory 220 may load the corresponding computer program from the storage device 230 so that the instructions described to execute the operation of the present disclosure are processed by the processor 210. For example, the memory 220 may include a read only memory (ROM), a Random access memory (RAM), etc.

The storage device 230 may non-transitorily store the computer program and various data. The storage device 230 may be configured to include a nonvolatile memory such as a read only memory (ROM), an erasable programmable ROM (EPROM), an electrically erasable programmable ROM (EEPROM), a flash memory or the like, a hard disk, a removable disk, or any type of computer-readable recording medium well-known in the art to which the present disclosure pertains.

The communication interface 240 may be a wired/wireless communication module that supports wired/wireless communication.

The bus 250 provides a communication function between components of the computing device 200.

The computer program includes instructions executed by the processor 210, and is stored in a non-transitory computer readable storage medium, and the instructions make the processor 210 execute the operation of the present disclosure. The computer program may be downloaded through a network or sold in a product form.

The computer program according to an exemplary embodiment may include instructions that output a scan waveform for 1D scanning to the focus variable lens 112 of FIG. 1, and performs axial motion search of acquiring the 1D scanned image of the sample 200 of FIG. 2 through high-speed axial scanning using the focus variable lens 112 of FIG. 1.

The computer program may include instructions that perform sample movement estimation of estimating the axial amplitude cycle of the sample 200 of FIG. 2 from the axial motion waveform of the sample 200 of FIG. 2 included in the 1D scanned image.

The computer program may include instructions that receives the ECG signal measured from the sample 200 of FIG. 2, extracts the heartbeat cycle from the ECG signal, generates a driving signal one cycle of a sample movement estimated for each heartbeat cycle, and outputs the generated driving signal to the focus variable lens 112 of FIG. 1, and varies the focal plane according to the sample movement according to the driving signal to perform a movement compensation of acquiring sample images at a moment when the sample movement and the focal plane are matched.

Hereinafter, the present disclosure will be described in detail through an experimental example. The experimental example is only for exemplifying the present disclosure, and the present disclosure is not limited thereto.

Experimental Example

An imaging condition is optimized to an intravital experiment. An image size is 256×256, and a frame speed is 27.7 frames per second (FPS).

A pinhole diameter of a confocal microscopy is 1 AU, an excitation wavelength of an axial motion probing mode is 488 nm, and an on-sample power is 1 to 1.5 mW.

As the focus variable lens, an ETL of Optotune AG is used. The ETL scanned a sample with an amplitude of 200 um at 55.4 Hz which is twice of the frame speed. Two periods of each ETL scanning may be included in a single image.

The ETL may achieve high-frequency dynamic focusing due to a rapid response time and a high frequency response bandwidth.

As the sample, a normal Balb/c mice was used, and a signal emitted from a rhodamine 6G label cell of the carotid artery was detected.

Before performing the intravital imaging, the axial motion probing mode, the movement estimation algorithm, and the movement compensation algorithm were tested by using a mirror sample.

During the axial motion probing mode, the ETL scans a moving sample at 40 to 100 Hz in an axial direction. In addition, a sample movement may be estimated from an acquired image.

When the sample movement is estimated, a reconfigured sample movement is transmitted to the ETL again, and a focus of the ETL is maintained on the moving sample.

A signal to the ETL is triggered by the ECG signal to match a timing of an estimated movement and an actual movement of the sample.

Since a motion artifact by heartbeat is severe when capturing an in vivo image of the carotid artery, the ECG signal is used to cause an operation of the ETL.

A dynamic focus approach scheme was verified by performing in vivo imaging of a mice carotid artery. An inter-frame transverse movement is completed by an intersection correlation algorithm for a reference frame. Accordingly, axial motion and lateral movement artifacts due to a unique tissue movement during in vivo imaging may be reduced by using a proposed method.

A quantitative analysis before/after movement compensation was also performed. An axial motion measurement algorithm using the ETL by scanning a moving tissue at 40 to 100 Hz was designed.

The ETL serves to maintain the focal plane even in a moving sample.

Minimum invasive stabilization, which has little negative impact on the tissue, provides a more natural environment in the in vivo imaging.

A dynamic focusing system using the ETL may capture an image without a continuous movement in the moving tissue, easily installs the ETL in a microscopy system, and enhance an availability of a method by compatibility with an immersion objective lens.

Acquisition of an image of the artery tends to be interfered by motion artifacts such as heartbeat and vascular shade. In order to process the motion artifacts and verify the performance of a newly developed motion compensation technology, a validity check system and an in vivo imaging system were designed.

In order to implement the motion compensation technology, a validation system and an in vivo imaging system which are two completely different confocal microscopy systems are developed. In the validation system, the progress of a motion correction algorithm was confirmed with a customized confocal microscopy. The electrically tunable lens (ETL) was installed on a back focal plane by using a C-mount and an RMS thread adapter.

The ETL is tried to be placed as close as possible to the back focal plane of the objective lens, but the ETL may not be used due to stretching by the adapter. Accordingly, when focus movement was accompanied by a change in magnification, such an effect does not have a significant impact on movement search performance.

When image storing starts, a vertical synchronization (V-sync) pulse generated whenever collecting all frames is completed is transmitted to a DAQ system. The V-sync pulse triggers a signal which heads to an ETL driver and a piezoelectric (PZT) controller. Focus movement driven by the ETL may be operated simultaneously when image collection starts.

In order to examine the performance of the movement search algorithm, a reflection signal of a mirror surface and an automatic fluorescence signal of a lens paper are imaged.

When the sample is placed on a PZT stage, the axial motion of the sample may be controlled by any input signal. The ETL was mounted on the back focal plane of the objective lens by the same scheme as in the validation system.

The electrically tunable lens (ETL) is a liquid lens covered with two membranes.

Sophisticated current control using a voice coil actuator changes a curvature radius of a lens surface by pressing the membrane. Input current to the ETL controls a subtle pressure applied to a voice coil bobbin which changes a curvature radius of an upper lens membrane.

According to Equation 4, a focal distance f is a function of curvatures of lenses R1 and R2.

$$\frac{1}{f} = \left(n - 1, \frac{1}{R_1} - \frac{1}{R_2}\right) \quad \text{(Equation 4)}$$

Accordingly, the focal distance may be adjusted by changing a shape of the lens. Focal distance modulation of several millimeters to hundreds of micrometers is possible according to the objective lens by inputting low current of 0 to 250 mA. Axial scanning which is much faster than the movement of the sample may collect the images even during the movement of the sample.

Axial Motion Probing Mode

FIGS. 15A and 15B illustrate principles of an 1D scanned image.

In this case, FIG. 15A illustrates a direction of a scanning mirror for generating an ordinary 2D image, and FIG. 15B illustrates a 1D scanned image for a fixed sample.

FIG. 15A illustrates a fluorescence image acquired by capturing the lens paper with the microscopy. In general, the lens paper as a soft material tissue for cleaning the lens was used as a fluorescence phantom having a fluorescence standard sample or structure in the experimental example.

Since a fluorescence image having a specific structure may be obtained by enlarging and observing the lens paper, the lens paper is used as a standard sample for obtaining and evaluating the fluorescence image.

As illustrated in FIG. 15A, an ordinary 2D image are generated through high-speed scanning and low-speed scanning, respectively by two scanning mirrors.

In this case, in high-speed axial scanning, a counter rotating scanner (CRS) may be used. Accordingly, when the 2D image is generated as illustrated in FIG. 15A, a part to which the high-speed scanning is applied may be referred to as CRS scanning.

In low-speed axial scanning, a galvano mirror may be used. Accordingly, a low-speed scanning interval in which scanning is performed at a relatively low speed as illustrated in FIG. 15A may be referred to as galvano scanning.

In the experimental example, unlike the generation of the ordinary 2D image, 1D scanning of driving only one scanning mirror between two scanning mirrors was performed, and a high-speed axial scanning direction was sampled through the 1D scanning. In this case, the 1D scanning was performed by driving only the CRS more suitable for high-frequency scanning compared to the galvano mirror. That is, during the 1D scanning, the galvano mirror is not operated, but only the CRS scans the sample.

FIG. 15B illustrates a 1D scanned image acquired through axial scanning while executing the galvano mirror is stopped, and the lens paper which fixes the sample not to move in the axial direction is imaged.

By such a scheme, a sampling point for the axial motion is represented by a continuous horizontal line having a sample frequency which is the same as a CRS driving frequency.

Since the lens paper in FIG. 15A is fixed to the axial direction, the 1D scanned image in which the horizontal is not changed overtime may be obtained in FIG. 15B. That is, the image is not changed according to the vertical direction.

Assumed that the size of the image is 1024×1024 and the CRS frequency is 4000 Hz, 1024/4000=0.256 s seconds is required for filling 1024 horizontal lines in the image. In this case, the frame speed is calculated as 1/0.256=3.9 frames per second (FPS). Consequently, the galvano mirror scans the sample at a frequency of 3.9 Hz according to the image size and the CRS frequency.

As such, since 0.256 seconds is required to form the image, sampling points for 0.256 seconds are stored in one image. Accordingly, a temporal change of a focal plane deviation between samples during the entire image acquisition period may be stored in the 1D scanned image.

FIGS. 16A, 16B, 16C and 16D are an exemplary diagram illustrating generation of a virtual 1D scanned image in a simulation.

FIG. 16A is a graph illustrating a temporal change of a focal plane position of a microscopy and an axial position of a sample according to one example, and FIG. 16B illustrates a 1D scanned image acquired through FIG. 16A.

According to FIG. 16A, a sample position moves vertically along a sinusoidal wave (or sine wave). When it is assumed that the focal plane of the microscopy is not changed over time, the focal plane position (or focus variable lens amplitude) of the microscopy is shown in a straight line.

In this case, when the 1D scanning mode is applied, a peak pixel intensity (or maximum pixel brightness value) is formed while the focal plane and the sample position are matched with each other.

According to FIG. 16B, a brighter horizontal line (or parallel line) than a surrounding area indicates a moment when the focal plane position and the position of the sample are matched with each other. In this case, the vertical line of the 1D scanned image indicates the time axis.

However, when the focal plane is fixed, a sufficient number of sampling points which may reconfigure the waveform may not be obtained. Therefore, due to the theorem of Nyquist, the sample should be scanned in the axial direction at least twice as fast as an axial motion frequency of an axial scanner, which is why the ETL should be used as essential.

FIG. 16C is a graph illustrating a temporal change of a focal plane position of a microscopy and an axial position of a sample according to another example, and FIG. 16D illustrates a 1D scanned image acquired through FIG. 16C.

The sample is scanned in the axial direction by using the ETL at a speed much faster than the motion of the sample, for example, 40 Hz to 100 Hz.

According to FIG. 16C, it is illustrated that the sample moves along the sinusoid wave (or sine wave), and the focal plane moves along a 40-Hz sawtooth wave. In this case, the peak pixel intensity is formed while the focal plane and the sample position are matched with each other.

According to FIG. 16D, a brighter horizontal line (or parallel line) than a surrounding area indicates a moment when the focal plane position and the position of the sample are matched with each other, and a plurality of horizontal lines are acquired. In this case, the vertical line of the 1D scanned image indicates the time axis. As such, a sufficient number of sampling points may be stored during 1D scanning.

The 1D scanned image illustrated in FIG. 16D is used to reconfigure a motion waveform the sample in the motion estimation mode.

Motion Estimation Mode

The 1D scanned image acquired through FIGS. 16B and 16D includes the sampling point for the axial motion, which may reconfigure the motion waveform of the sample.

Figure 17A:
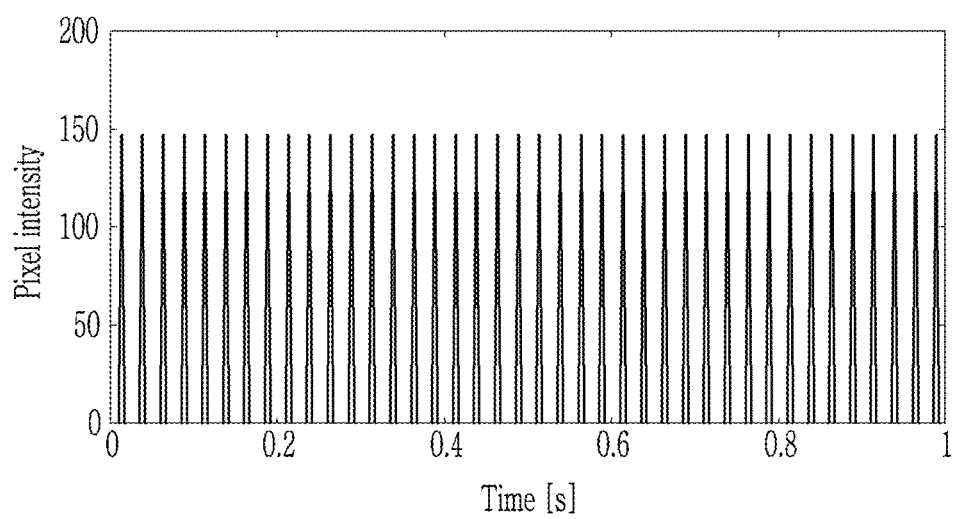
FIGS. 17A, 17B, and 17C illustrate a simulation process for estimating axial motion of a sample.
Figure 17B:
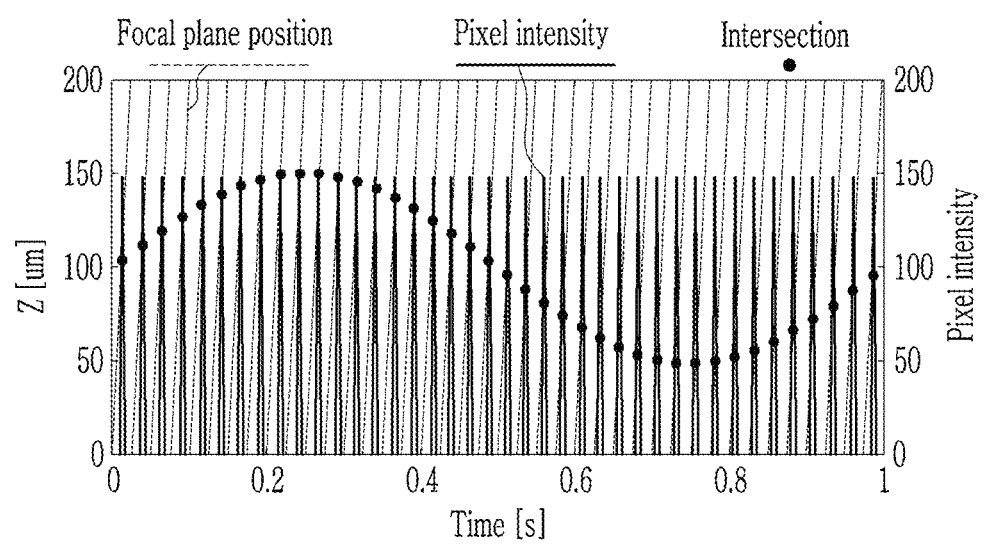
Figure 17C:
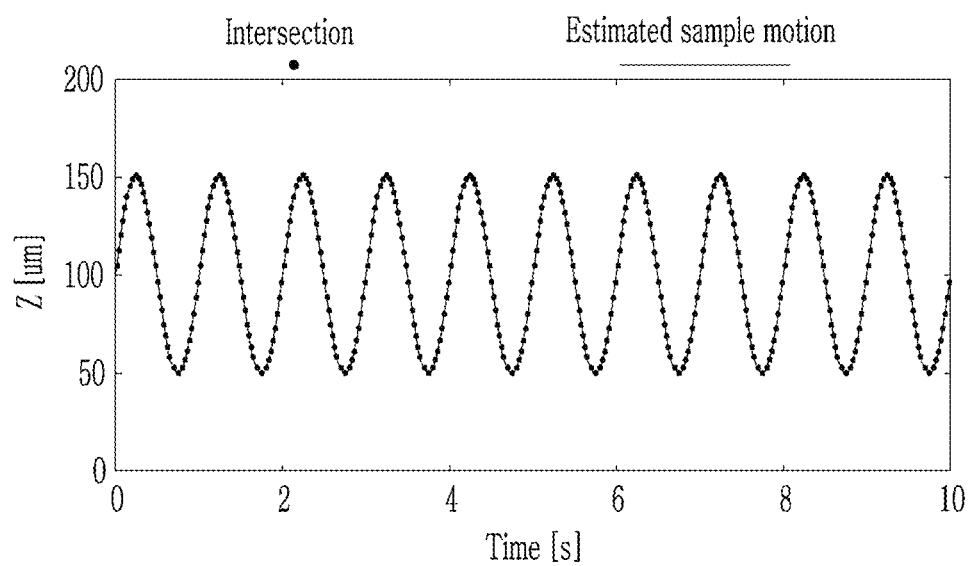

FIGS. 17A, 17B, and 17C illustrate a simulation process for estimating axial motion of a sample.

In this case, FIG. 17A illustrates a temporal change of pixel intensity data according to the elapse of time. FIG. 17B is a graph illustrating a temporal change of the focal plane position and the axial position of the sample of the microscopy. FIG. 17C is a graph illustrating the reconfigured motion waveform of the sample.

Continuous 1D scanned images may be jointly disposed on the time axis, and the pixel intensity data according to the time may be illustrated as in FIG. 17A. The pixel intensity data are acquired on vertical lines of the continuous 1D scanned images displayed in FIGS. 16B and 16D.

According to FIG. 17B, the focal plane position of the microscopy is expressed as the 40-Hz sawtooth wave. Since information on the input signal for the ETL, e.g., a sawtooth waveform, an amplitude, and a frequency are known, a focal plane motion by the ETL is expressed as the sawtooth waveform as in FIG. 17B based on thereon.

In this case, a point where the pixel intensity data and the focal plane position intersect includes motion information of the sample. Since the peak pixel intensity is reached only while the position of the sample and the focal plane are matched with each other, an interaction point of the focal plane change and the temporal pixel intensity change derived by the ETL becomes the sampling point of the sample waveform.

Accordingly, the motion waveform of the sample according to the time may be estimated as illustrated in FIG. 17C through a task of matching with the continuous 1D scanned images.

However, the motion waveform of the sample was estimated, assuming that there was only one intersection point during each period of the change in sawtooth waveform of the focal plane by the theory of an intermediate value. In other words, in the focal plane matching process illustrated in FIG. 17B, starting points of the temporal pixel intensity change and the focal plane change are just known, and it is assumed that the temporal pixel intensity change and the focal plane change are started to be the same. An error of the starting point causes the amplitude offset as described in FIG. 11 above.

Besides, the amplitude error, the phase offset, and the frequency error cause a difference between an actual sample motion and an estimated sample motion waveform, and the user manually adjusted the amplitude offset, the amplitude error, and the phase offset while viewing the image acquired in real time, and the frequency error was solved by triggering the focal plane movement through the heartbeat.

Another important consideration for sample motion compensation is that a fluorescent sample has a wide axial response. For example, the mirror sample generates a vivid and bright horizontal line in the 1D scanned image, while a fluorescent sample such as an autofluorescence of the lens paper or tissue in the in vivo imaging generates a thick and wide horizontal line in the 1D scanned image. Consequently, an accurate axial position of the focus may not be determined in a wide and bright horizontal line.

When the axial sample motion is probed by using only the peak pixel intensity, a combination of other focal planes interferes with the accuracy of the motion estimation. Therefore, an additional correction algorithm is implemented in order to correct an intersection error between an actual focus and a focus with an error.

According to the additional correction algorithm, first, a single bright focus line is acquired in the peak pixel intensity horizontal line within each axial scan period in the 1D scanned image. By the theory of the intermediate value described above, one bright focus line exists in the axial scan period. For example, when the sample is scanned on a 40-Hz axis in the 1D scan mode, 40 bright focus lines are displayed.

A single virtual focus is obtained, which averages all bright focus lines. The virtual focus is closer to the actual focus compared to the focus line discovered only with the bright pixel intensity. Then, an intersection correlation between the virtual focus and the continuous 1D scan image is calculated. That is, a horizontal line most similar to the virtual focus may be found by using the intersection correlation calculation. Consequently, a more accurate axial position of the sample may be determined.

Correcting the focus with the single virtual focus may not be suitable for high-performance motion estimation. For this reason, adjacent horizontal lines are included in the generation of the virtual focus.

In a first step, in order to find the virtual focus, the single bright focus line of each axial scan period was determined, and used for averaging.

In order to add adjacent horizontal lines, two horizontal lines above the bright focus line and two horizontal lines below the bright focus line are selected. Therefore, a focus image is generated, which is constituted by five horizontal lines instead of one bright focus line.

A subsequent process is the same as correction of the single bright focus line. The focus image is averaged with respect to each axial scan period, and then the virtual focus image is obtained.

The virtual focus image is used for mutual correlation calculation between the continuous 1D scanned images in order to find a focal plane most similar to the virtual focus image. By such a scheme, a focus line with misunderstanding may be modified to the actual focus line.

As such, when the focus correction algorithm using the virtual focus image is used, the accuracy of determination of the focus plane position may be increased up to ±0.768 um.

As mentioned above, the reason for finding the focus line in the 1D scanned image is to find an accurate intersection point as possible, that is, the intersection point illustrated in FIG. 17B.

In the case of the mirror, the bright horizontal line is generated only while the mirror surface and the focal plane are matched with each other in the 1D scanned image. On the contrary, in the case of a thick fluorescent sample, the bright horizontal line of the 1D scanned image may be generated, and the focal plane is not accurately matched even on a mirror surface. This is because the focus is on the wide axial response of the fluorescent sample, that is, the sample focuses on a wide axial depth. Accordingly, it is difficult to designate one focal plane in the fluorescent sample. For this reason, the intersection correlation was calculated in order to obtain the virtual focus image, and specifically determine the focal plane. Since the intersection correlation outputs how similar two data are, one focal plane may be determined in a thick axial response fluorescent sample. Therefore, an estimated waveform which may be obtained through the motion estimation algorithm is an axial motion at a position designated by the virtual focus.

Figure 18A:
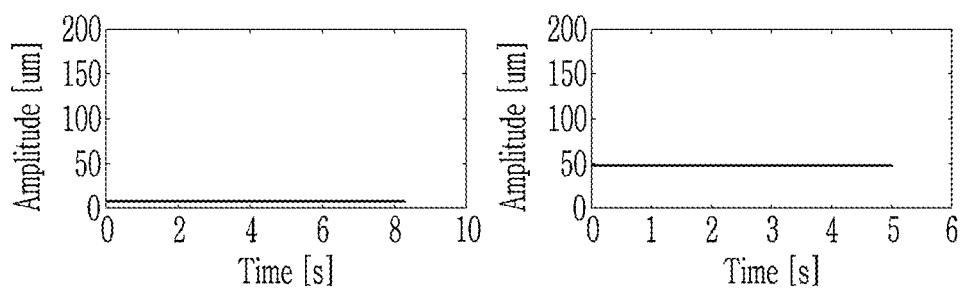
FIGS. 18A, 18B and 18C illustrate a displacement of a mirror sample measured through movement estimation.
Figure 18B:
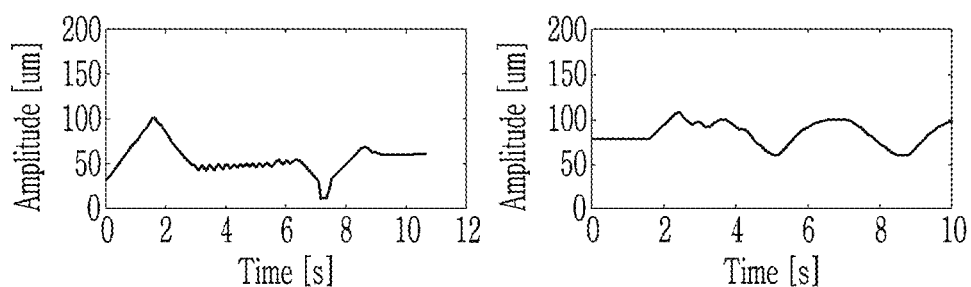
Figure 18C:
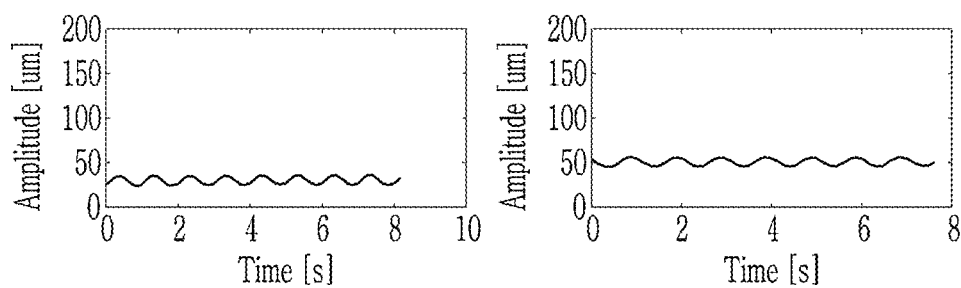

FIGS. 18A, 18B and 18C illustrate a displacement of a mirror sample measured through movement estimation.

FIG. 18A illustrates a stop operation in which a standard deviation is less than 500 nm when a mirror sample stops.

In FIG. 18B, the mirror was manually moved in the axial direction by using a piezoelectric stage. Motion estimation may randomly reconfigure the sample motion.

In FIG. 18C, a repeated sample motion which moves with a 1-Hz sinusoid wave was estimated.

In a result of FIG. 18, the amazing performance of the motion estimation may be seen.

When the scanning range of the ETL increases, a sample motion which is larger than 200 μm may also be estimated. A time required for estimating the sample motion is very important in the in vivo imaging. It takes approximately 30 seconds to acquire and store the 1D image, and it takes 10 to 20 seconds to calculate the axial motion with the motion estimation process.

It may takes a longer time depending on the number of 1D images to be analyzed, but in most cases, it takes less than 1 minute to find the axial motion of the sample. Fast elapse time for motion estimation is very important for using an algorithm during the in vivo imaging.

When an anesthesia period is longer, the long anesthesia period is a high death risk for mice and the possibility of survival after the experiment decreases. In addition, when the motion estimation process takes a long time, the estimated motion may be different from the actual movement.

FIGS. 19A, 19B, 19C and 19D illustrate a result of a movement estimation process for the mice carotid artery.

Figure 19B:
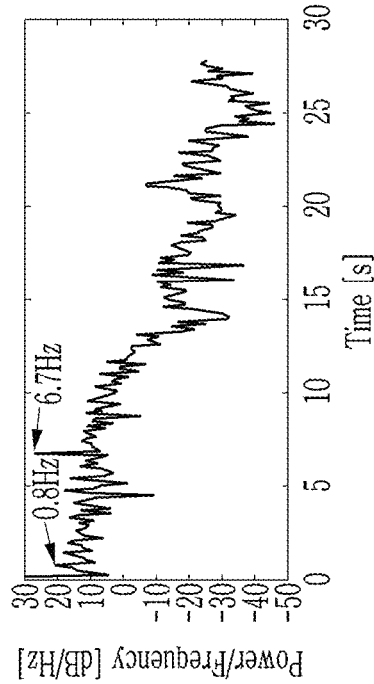
FIGS. 19A, 19B, 19C and 19D illustrate a result of a movement estimation process for the rat carotid artery.
Figure 19D:
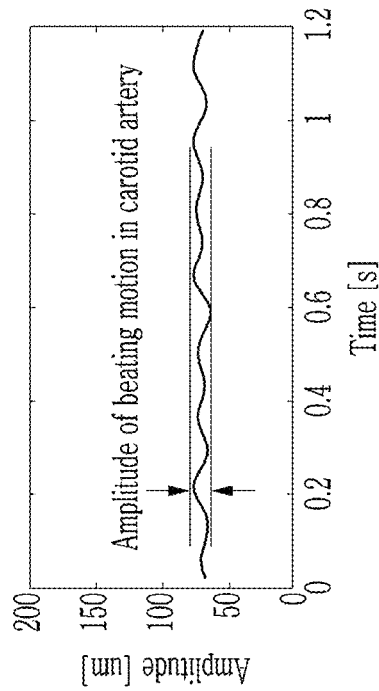
Figure 19A:
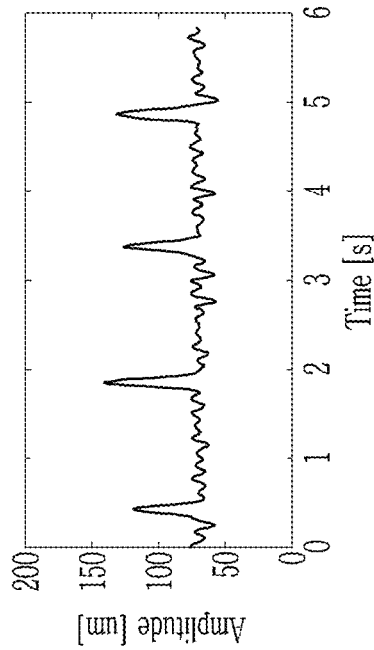
Figure 19C:
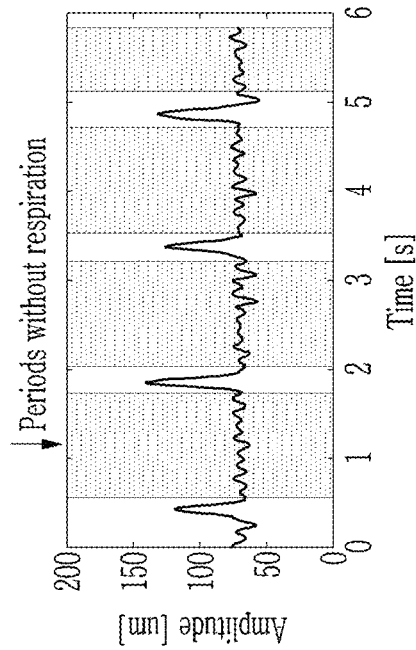

FIG. 19A illustrates an axial displacement of the carotid artery, FIG. 19B illustrates a spectrum density for a sample motion calculated, FIG. 19C illustrates a selected period of not receiving breathing, and FIG. 19D illustrates an amplitude and a waveform in a selected cycle.

An axial motion of the mice carotid artery measured by using the motion estimation process is illustrated in FIG. 19A. It can be seen that an overall motion of the artery is constituted by the breathing and the heartbeat.

The axial displacement is larger in the breathing than in the hear beat, but focuses on compensating the motion due to the heartbeat. The reason is that when an ECG board is used, a timing signal may be easily obtained from a heartbeat signal, but it is difficult to obtain the timing signal for the breathing.

A power spectrum density for the estimated carotid artery motion is illustrated in FIG. 19B. Two high peaks at 0.8 Hz and 6.7 Hz represent frequencies of the breathing and the heartbeat. This result is matched with a tissue motion measured by using a laser displacement sensor such as Lee, etc., and peaks of 1 Hz and 6 Hz which are the heartbeat and breathing frequencies, respectively are observed.

By a user interface of the motion estimation algorithm, the axial displacement due to the heartbeat may be manually selected. In FIG. 19C, one of the periods when the breathing does not appear is selected.

A selective operation range including only the motion due to the heartbeat is expressed in FIG. 19D. In this plot, the amplitude and waveform of the movement may be identified. When the amplitude and the waveform are known, the waveform is cut and transmitted to the ETL in a single cycle, and triggered by ECG heartbeat.

Motion Reconstruction Mode

A single-cycle waveform triggered by the ECG heartbeat was generated as a driving signal, and transmitted to the ETL, which allowed the focal plane of the ETL to move according to the motion of the sample, and an in vivo image of a sample with a compensated motion was acquired so as to match the sample motion through the moving focal plane.

When the single cycle of the waveform is obtained from the motion estimation algorithm, it may be analyzed how close the focal plane may be maintained to the beating carotid artery.

Figure 20:
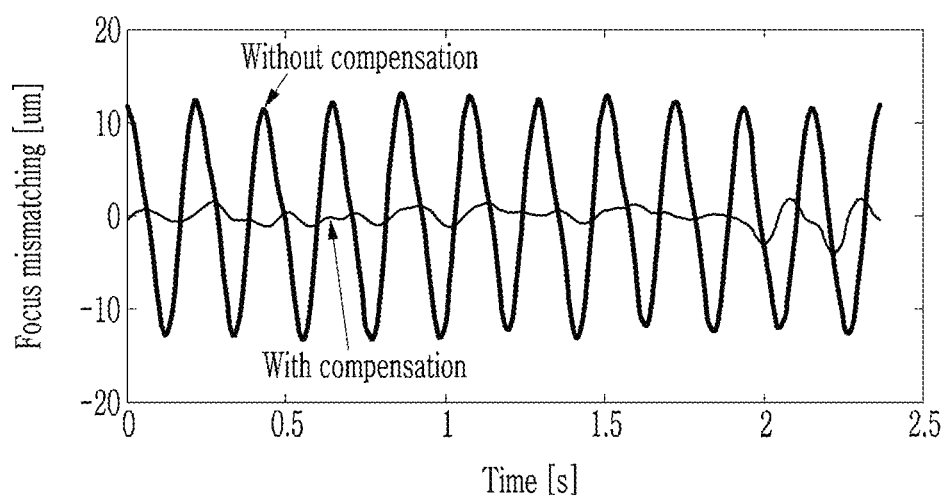
FIG. 20 illustrates a simulation result for focus mismatch between a focal plane without correction with a sample or a focal plane with correction with the sample.

FIG. 20 illustrates a simulation result for focus mismatch between a focal plane without correction with a sample or a focal plane with correction with the sample.

The simulation result of FIG. 20 represents a value acquired by subtracting an average of displacements from measurement data (without compensation), and a value acquired by subtracting each prediction motion cycle from measurement data (with compensation).

When the focal plane is fixed, the carotid artery continuously moves away from the focal plane due to the heartbeat. A standard deviation for the mismatch is calculated as 8.45 um.

Since an axial response of the microscopy system is less than 14 μm in a state in which the ETL is installed, the image is severely damaged by motion artifacts due to the displacement of the heartbeat. On the contrary, when the focal plane dynamically moves along the sample as the estimated sample motion, a focus mismatch within 1 um may be maintained. Accordingly, the axial motion may be effectively compensated in the axial response of the system.

This result is an ideal case for motion compensation, but may be surely reproduced when the estimated sample motion is sufficiently accurate, and the trigger signal is stably generated.

In order to generate an estimation operation whenever the heartbeat signal is triggered, stable and repeated ECG signals should be generated in the ECG board.

According to the measurement, a beating rate of the mice was approximately 420 to 600 times per minute. Each time the heartbeat cycle arrives, an expected carotid artery movement obtained in FIG. 19D may be generated.

PSL-iECG2 used to generate the ECG and heartbeat signals is for humans. Accordingly, an LPF and notching filtering were optimized to stably generate the signal from the mice. The heartbeat signal using the ECG board is sufficiently applied to an operation compensation concept.

Figure 21A:
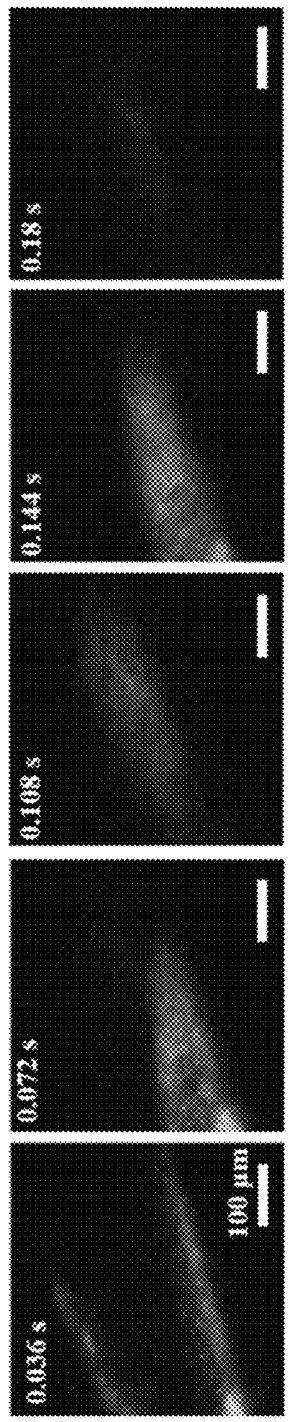
FIGS. 21A and 21B illustrate a series of images with or without movement correction obtained from the rate carotid artery.
Figure 21B:
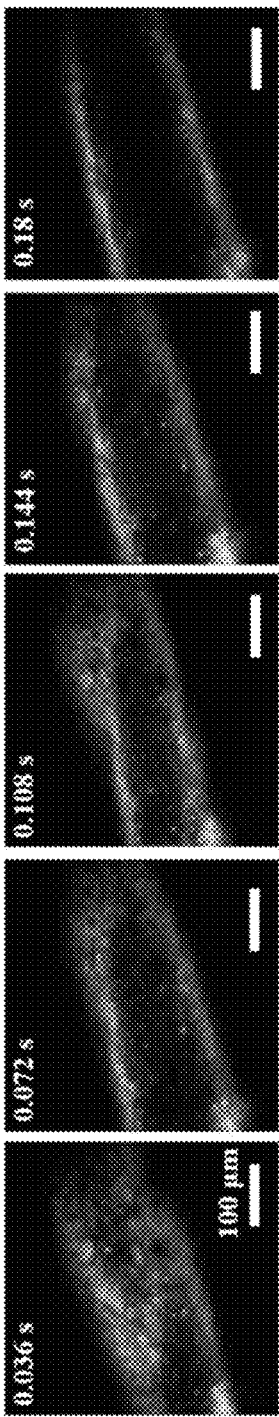

FIGS. 21A and 21B, which illustrate a series of images with or without motion correction, which is obtained from the mice carotid artery, illustrates sequential intravital images obtained a 20× immersion objective lens in 14.6 FPS. An image size is 512×512.

FIG. 21A illustrates a mice carotid artery image without the motion correction. FIG. 21B illustrates a mice carotid artery image with the motion correction. The image is acquired from the same region of interest.

In this case, the same region of interest was imaged, and a dynamic focal plane was disposed inside the artery.

Results before and after the motion correction which moves the focal plane according to the motion by the heartbeat in the carotid artery are illustrated in FIG. 21.

According to FIG. 21A, the focal plane continuously deviates from the inside of the artery due to the motion by the heartbeat before the motion correction, while according to FIG. 21B, the focal plane may be maintained inside the artery even though the carotid artery moves after the motion correction.

That is, when there is no motion correction, the focal plane is fixed, but when the motion correction is turned on, the focal plane moves along carotid artery movement. It can be seen that since the focal plane goes out of the carotid artery, a large deviation between frames is observed without the motion correction, while the focus may stay inside the carotid artery for a longer time.

It can be seen that since the motion artifacts derived by both the heartbeat and the breathing are severe, it is also impossible to apply cell tracking to the frame without the motion correction. Individual cells which flow inside the carotid artery may be seen in FIG. 21B.

Figure 22A:
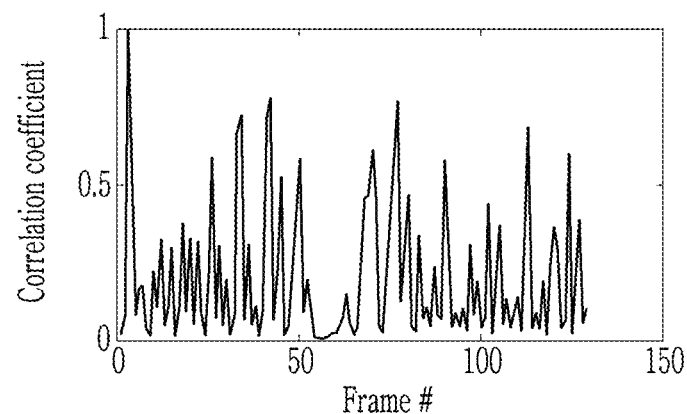
FIGS. 22A, 22B, and 22C illustrate a result of quantitatively analyzing a moment of being in focus between a case where there is no movement compensation and image acquisition for the case where there is no movement compensation.
Figure 22B:
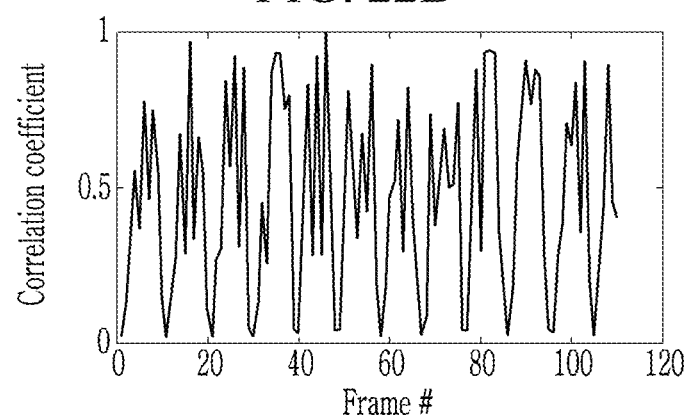
Figure 22C:
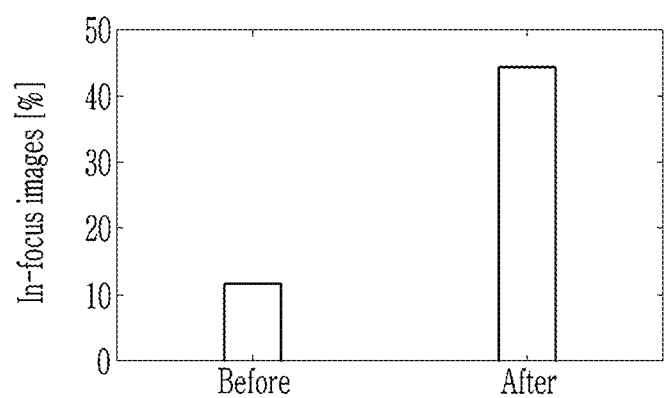

FIGS. 22A, 22B and 22C, which illustrate that a moment when a case without the motion correction and image acquisition for the case without motion correction are in focus is quantitatively analyzed, illustrates a result of calculating a correlation coefficient for a manually selected frame, and a focus frame manually selected is used for calculating correlation coefficients for the remaining image sets.

FIG. 22A illustrates the case without the motion correction, FIG. 22B corresponds to a case with the motion correction, and FIG. 22C illustrates a percentage of an image in which the correlation coefficient is larger than 0.5.

When the correlation coefficient is close to 1, the image is similar to a reference image. Accordingly, the more images in which the correlation coefficient is close to 1 are, the more often the focus frame is included in an image set.

According to FIG. 22A, in a case where the focal plane does not move along the sample, that is, in the case of a non-correction mode, most images are not similar to the reference image due to the motion artifacts.

According to FIG. 22B, after the focal plane follows the axial motion of the carotid artery, more images may be found in which the correlation coefficient is close to 1. Some images are still influenced by the motion artifact by the breathing. Then, images in which the correlation coefficient is larger than 0.5 were selected in the case without the motion correction and the case with the motion correction.

According to FIG. 22C, the result is shown. Before the motion correction, 11.6% of images in the image set has a correlation coefficient larger than 0.5 with respect to the reference image. After the motion correction, 44.5% of the images in the image set satisfy a condition. Such a result shows that the number of images which are in focus increases four times more after the motion correction.

An enhancement degree of a time solution is definitely important. The individual cells which flow inside the artery may be definitely displayed due to the high performance of the motion correction technology, and cell tracking analysis which was impossible without the motion correction may be ensured.

The exemplary embodiments of the present disclosure described above is not implemented only through the apparatus and the method and can be implemented through a program which realizes a function corresponding to a configuration of the exemplary embodiments of the present disclosure or a recording medium having the program recorded therein.

While the present disclosure has been described in connection with what is presently considered to be practical exemplary embodiments, it is to be understood that the invention is not limited to the disclosed exemplary embodiments, but, on the contrary, is intended to cover various modifications and equivalent arrangements included within the spirit and scope of the appended claims.

What is claimed is:

1. A method for capturing in vivo images by a control device which operates by at least one processor, comprising:
   acquiring 1dimensional (D) images acquired by scanning in vivo samples in one direction from a confocal microscopy including a focus variable lens;
   estimating motion information of the in vivo sample from the 1D images;
   generating a driving signal for synchronizing and varying a focal plane of the focus variable lens with a motion of the in vivo sample based on the estimated motion information, and controlling the focus variable lens with the driving signal; and
   acquiring, from the confocal microscopy, continuous images of the in vivo sample scanned in the focal plane varied according to the driving signal.

2. The method of claim 1, wherein:
   in the estimating,
   an axial motion waveform of the in vivo sample is generated through the 1D images, and an axial amplitude cycle acquired from the axial motion waveform is estimated as the motion information.

3. The method of claim 2, wherein:
the estimating includes,
generating one image acquired by frame-unit 1D images in a time-axis direction,
acquiring pixel brightness information according to time from the merged image, and
estimating the axial amplitude cycle of the in vivo sample by using sampling points which are points where the waveform of driving the focus variable lens and the pixel brightness information intersect when scanning the 1D images.

4. The method of claim 1, wherein:
in the controlling,
a driving signal generated by using waveform information of a predetermined unit cycle confirmed from the estimated motion information is output to the focus variable lens.

5. The method of claim 4, wherein:
in the controlling,
a driving signal is generated, in which a one-cycle waveform of the sample motion confirmed from the estimated motion information is converted into a voltage unit.

6. The method of claim 1, further comprising:
between the estimating and the controlling,
receiving an electrocardiogram signal measured from the in vivo sample by an electrocardiogram measurement device, from the electrocardiogram measurement device,
wherein in the controlling,
the driving signal is generated every heartbeat cycle acquired from the electrocardiogram signal, and output to the focus variable lens.

7. The method of claim 6, wherein:
in the controlling,
motion information of one cycle corresponding to the heartbeat cycle is acquired from the estimated motion information of the in vivo sample, and a driving signal is generated, in which the acquired motion information is converted into the voltage unit.

8. The method of claim 1, wherein:
the focus variable lens,
includes an electrically tunable lens (ETL).

9. A control device comprising:
a memory storing instructions for performing an control operation for capturing an in vivo image; and
at least one processor executing the instructions,
wherein the at least one processor
acquires 1D images for scanning in vivo samples in one direction from a confocal microscopy including a focus variable lens, and estimates motion information of the in vivo sample from the 1D images, and
controls the focus variable lens by using a driving signal for synchronizing and varying a focal plane of the focus variable lens generated based on the estimated motion information with a motion of the in vivo sample, and acquires continuous images of the in vivo sample scanned on the focal plane varied according to the driving signal, from the confocal microscopy.

10. The control device of claim 9, wherein:
the at least one processor,
analyzes a heartbeat cycle from an electrocardiogram signal measured from the in vivo sample, and outputs the driving signal to the focus variable lens whenever the heartbeat cycle arrives.

11. The control device of claim 10, wherein:
the at least one processor,
generates an axial motion waveform of the in vivo sample through the 1D images, and generates the driving signal by converting a one-cycle waveform corresponding to the heartbeat cycle into a voltage unit at an axial amplitude cycle acquired from the axial motion waveform.

12. The control device of claim 9, wherein:
the at least one processor,
acquires pixel brightness information according to time from one image acquired by merging a plurality of frame-unit 1D images in a time-axis direction, and
estimates axial motion information of the in vivo sample by using sampling points which are points where the waveform of driving the focus variable lens and the pixel brightness information intersect when scanning the 1D images.

13. A system for capturing in vivo images, comprising:
a confocal microscopy generating 1D images by scanning in vivo samples in one direction by using a focus variable lens; and
a control device estimating motion information of the in vivo sample from the 1D images acquired from the confocal microscopy, generating a driving signal for synchronizing and varying a focal plane of the focus variable lens generated based on the estimated motion information with the a motion of the in vivo sample, controlling the focus variable lens with the driving signal, and acquiring continuous images of the in vivo sample scanned on the focal plane varied according to the driving signal, from the confocal microscopy.

14. The system for capturing in vivo images of claim 13, wherein:
the confocal microscopy includes,
the focus variable lens in which a focal plane is varied as a curvature radius is changed by input current, and
a scanning module generating the 1D images for the in vivo sample through 1D scanning which drives only an X-axis scanner, and outputting the generated 1D images to the control device.

15. The system for capturing in vivo images of claim 14, wherein:
the confocal microscopy further includes,
an objective lens refracting light irradiated by a light source and passing through the focus variable lens, and guiding the refracted light to the in vivo sample, and absorbing light reflected on the in vivo sample, and delivering the absorbed light to the scanning module, and
the focus variable lens,
is attached to a back focus plane of the objective lens.

16. The system for capturing in vivo images of claim 14, further comprising:
a photo multiplier tube converting optical signal type images acquired through a scan operation of the scanning module into an electrical signal, and outputs the converted images to the control device.

17. The system for capturing in vivo images of claim 13, wherein:
the control device,
generates an axial motion waveform of the in vivo sample through the 1D images, and generates the driving signal by converting a predefined unit cycle waveform into a voltage unit at an axial amplitude cycle acquired from the axial motion waveform.

18. The system for capturing in vivo images of claim 13, further comprising:
an electrocardiogram measurement device measuring an electrocardiogram (ECG) of the in vivo sample,
wherein the control device
analyzes a heartbeat cycle from an electrocardiogram signal received from the ECG measurement device, and outputs the driving signal to the focus variable lens whenever the heartbeat cycle arrives.

19. The system for capturing in vivo images of claim 18, wherein:
the control device,
acquires pixel brightness information according to time from one image acquired by frame-unit 1D images in a time-axis direction,
estimates the axial amplitude cycle of the in vivo sample by using sampling points which are points where the waveform of driving the focus variable lens and the pixel brightness information intersect when scanning the 1D images, and
converts a one-cycle waveform corresponding to the heartbeat cycle during the estimated axial amplitude cycle into a voltage unit to generate the driving signal.

20. The system for capturing in vivo images of claim 19, further comprising:
a data-signal integration device receiving the scanned images from the confocal microscopy, and delivering the received images to the control device, delivering the ECG signal received from the ECG measurement device to the control device, and outputting the driving signal to the focus variable lens.

* * * * *